(12) United States Patent
Yanagawa et al.

(10) Patent No.: US 6,361,943 B1
(45) Date of Patent: Mar. 26, 2002

(54) MOLECULE THAT HOMOLOGIZES GENOTYPE AND PHENOTYPE AND UTILIZATION THEREOF

(75) Inventors: Hiroshi Yanagawa; Naoto Nemoto, both of Machida; Etsuko Miyamoto, Yokohama; Yuzuru Husimi, Urawa, all of (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/284,627

(22) PCT Filed: Oct. 17, 1997

(86) PCT No.: PCT/JP97/03766

§ 371 Date: Jun. 2, 1999

§ 102(e) Date: Jun. 2, 1999

(87) PCT Pub. No.: WO98/16636

PCT Pub. Date: Apr. 23, 1998

(30) Foreign Application Priority Data

Oct. 17, 1996 (JP) .............................. 8-274855

(51) Int. Cl.[7] .......................... C12Q 1/68; C07H 21/02; C07H 21/04; C07K 1/00; C12P 21/06; G01N 33/53

(52) U.S. Cl. .......................... 435/6; 435/7.1; 435/69.1; 530/350; 536/23.1; 536/24.2; 536/25.3

(58) Field of Search .............................. 435/6, 69.1, 7.1; 536/23.1, 24.2, 25.3; 530/350

(56) References Cited

U.S. PATENT DOCUMENTS 5,843,701 A * 12/1998 Gold et al. ................. 435/68.1

FOREIGN PATENT DOCUMENTS

| DE | 196 46 372 | 6/1997 |
|----|------------|--------|
| WO | 95/11922 | 5/1995 |
| WO | 96/22391 | 7/1996 |
| WO | 98 31700 | 7/1998 |

OTHER PUBLICATIONS

Y. Husimi et al., "Role of the virus–type strategy in encoded molecular evolution", Progress in Biophysics and Molecular Biology, vol. 65, Suppl. 1, p. 64, Aug. 1996.

(List continued on next page.)

Primary Examiner—Robert A. Schwartzman
Assistant Examiner—Katharine F Davis
(74) Attorney, Agent, or Firm—Wenderoth, Lind & Ponack, L.L.P.

(57) ABSTRACT

A molecule comprising a nucleic acid portion and a protein portion directly bound to said nucleic acid portion with a covalent bond, wherein said nucleic acid portion comprises a polymer of nucleoside, and said protein portion is encoded by said nucleic acid portion, and a method for constructing the molecule, which comprises (a) preparing a DNA containing a gene which has no termination codon, (b) transcribing the prepared DNA into RNA, (c) bonding a chimeric spacer composed of DNA and RNA to a 3'-terminal end of the obtained RNA, (d) bonding to a 3'-terminal end of the obtained bonded product, a nucleoside or a substance having a chemical structure analogous to that of a nucleoside, which can be covalently bound to an amino acid or substance having a chemical structure analogous to that of an amino acid, and (e) performing protein synthesis in a cell-free protein synthesis system using the obtained bonded product as mRNA to bond a nucleic acid portion containing the gene to a translation product of the gene. The molecule of the present invention is an extremely useful substance that can be used for evolutionary molecular engineering, i.e., modification of functional biopolymers such as enzymes, antibodies, and ribozymes, and creation of biopolymers having functions which cannot be found in living organisms.

24 Claims, 11 Drawing Sheets

STRATEGY FOR ASSIGNING GENOTYPE TO PHENOTYPE

Genotype and phenotype:
Carried on the same molecule

Form complex

Contained in single compartment

Strategies for assignment are logically classified into three patterns.

OTHER PUBLICATIONS

N. Nemoto et al., "In vitro virus: Bonding of mRNA bearing puromycin at the 3'terminal end to the C–terminal end of its encoded protein on the ribosome in vitro", FEBs Letters, vol. 414, No. 2, pp. 405–408, Sep. 1997.

J. K. Scott et al., "Searching for peptide ligands with an epitope library", Science, vol. 249, pp. 386–390, 1990.

S. Brenner et al., "Encoded combinatorial chemistry", Proc. Natl. Acad. Sci. USA, vol. 89, pp. 5381–5383, 1992.

Tung et al., Bioconjugate Chem. 6: 292–295, Dual–specificity interaction of HIV–1 TAR RNA with Tat peptide–oligonucleotide conjugates, 1995.*

* cited by examiner

STRATEGY FOR ASSIGNING GENOTYPE TO PHENOTYPE

Strategies for assignment are logically classified into three patterns.

1. "In vitro virus" genome

2. Cell-free translation system

3. Puromycin binds to polypeptide

4. Release from ribosome

"In vitro virus" virion

5. Selection process

US 6,361,943 B1

MOLECULE THAT HOMOLOGIZES GENOTYPE AND PHENOTYPE AND UTILIZATION THEREOF

BACKGROUND OF THE INVENTION

1. Technical Field

The present invention relates to a molecule assigning a genotype to a phenotype. More specifically, it relates to a molecule assigning a genotype to a phenotype, comprising a nucleic acid portion having a nucleotide sequence reflecting the genotype and a protein portion comprising a protein involved in exhibition of the phenotype. The molecule assigning the genotype to the phenotype of the present invention is a highly useful substance that can be utilized in evolutionary molecular engineering such as in the modification of enzymes, antibodies, ribozymes and other such functional biopolymers and creation of biopolymers having functions not found in living organisms.

Through advances in biochemistry, molecular biology and biophysics, it has been learned that living organisms are molecular machines which function and propagate by interactions among molecules. Among the characteristics of earth's living organisms, the fundamentals are their preservation of genetic information in DNA nucleotide sequences and their ability to translate this information into functional proteins through the medium of mRNA. Owing to progress in genetic engineering, biopolymers with given sequences, like nucleotides and peptides, can now be easily synthesized. Protein engineering and RNA engineering, today a focus of attention, owe their existence to genetic engineering. The aims of protein engineering and RNA engineering are to solve the puzzle of the three-dimensional structures required for proteins and RNA fulfilling specific functions and to enable humans to freely design proteins and RNA possessing desired functions. Because of the diversity and complexity of these structures and the difficulty of a theoretical approach to their three-dimensional structures, however, current protein engineering and RNA engineering are still at the stage of modifying some of residues at active sites and observing changes in the structure and functions. Human knowledge has thus not yet reached the stage of designing proteins and RNA.

Understanding the functions of biopolymers in their relationship to the elemental processes of higher life phenomena will require elucidation of the correlation between protein molecular structure and function. The line of thought we take in the following is not only to make the best of "human knowledge" but also to take advantage of the "wisdom of nature." This is because we concluded that we would have to acquire the ability to put both to work in order to overcome the current difficulties of protein engineering and move forward with the design and production of functional biopolymers. When the classical methods are diverted to the design of proteins with new functions and activities, the difficulty of protein design by site-specific mutations can sometimes be avoided. This can be called "taking advantage of the wisdom of nature."

Although the drawback of this method is the difficulty of screening to identify mutants with new functions and activities, this difficulty is overcome by the RNA catalysts that have recently come into the spotlight. Attempts have been made to select an RNA with specific characteristics from among RNAs synthesized to have an extremely large number of random sequences (about $10^{13}$ types) (Ellington, A. D. & Szostak, J. W. (1990) Nature, 346, 818–822).

This is an example of evolutionary molecular engineering. As typified by this example, the primary goal in the evolutionary molecular engineering of proteins is to find out optimum sequences by searching an expansive sequence space of a scale unimaginable in conventional protein engineering. By "making the best of human knowledge" to devise a screening system for this, it will be possible to discover numerous quasi-optimum sequences around the optimum sequences and thus to construct an experimental system for studying "sequence vs function."

The remarkable functions of living bodies were acquired through the process of evolution. Therefore, if evolution can be replicated, it should be possible to modify enzymes, antibodies, ribozymes and other functional biopolymers and, further, to create biopolymers with functions not found in living organisms in the laboratory. Needless to say, research on protein modification and creation is an object of utmost importance to various aspects of biotechnology such as utilization of enzymes as industrial catalysts, biochips, biosensors and sugar-chain engineering.

Given the fact that molecular design utilizing structural theory is, as symbolized by the continuing high regard for "screening," still in an unperfected state, the evolutionary technique has a practical value for utilization in selecting useful proteins as a more efficient strategy. Building a "time machine" capable of more efficiently producing evolution in a laboratory, if such were possible, would not only enable modification of enzymes, antibodies (vaccines, monoclonal antibodies etc.) and other existing proteins but also open the way to the creation of enzymes for decomposing environmental contaminants, purifiers and others and new proteins not present in the biological world. If an experimental system for protein evolution can be established, therefore, it can be expected to be aggressively utilizable for application in a wide range of fields including power saving and energy preservation in industrial processes, energy production and environmental preservation. The assigning molecule of the present invention is a highly useful substance in protein modification and other aspects of evolutionary molecular engineering.

2. Description of the Related Art

Evolutionary molecular engineering is a field of study that attempts to conduct molecular design of functional polymers by utilizing high-speed molecular evolution in the laboratory, i.e., by laboratory investigation and optimization of the adaptive locomotion of biopolymers in sequence space. It is a completely new molecular biotechnology that first produced substantial results in 1990 (Yuzuru Husimi (1991) Kagaku, 61, 333–340; Yuzuru Husimi (1992) Koza Shinka, Vol. 6, University of Tokyo Publishing Society).

Life is a product of molecular evolution and natural selection. The evolution of molecules is a universal life phenomenon but its mechanism is not something that can be elucidated by studies that track the history of past evolution. Rather, the approach of constructing and studying the behavior of simple molecules and life systems that evolve in the laboratory better provides fundamental knowledge regarding molecular evolution and enables establishment of a verifiable theory applicable in molecular engineering.

It is known that a polymer system will evolve if it satisfies the following five conditions: (1) an open system far out of equilibrium, (2) a self-replicative system, (3) a mutation system, (4) a system with genotype and phenotype assignment strategy, and (5) a system with appropriate adaptation topography in sequence space. (1) and (2) are conditions for occurrence of natural selection and (5) is determined beforehand by the physicochemical properties of the biopolymer. The genotype and phenotype assignment of (4) is a prerequisite for evolution by natural selection.

The following three strategies are adopted in both the natural world and evolutionary molecular engineering: (a) ribozyme-type in which the genotype and the phenotype are carried on the same molecule, (b) virus-type in which the genotype and the phenotype form a complex, and (c) a cell-type in which the genotype and the phenotype are contained in a single compartment (FIG. 1).

As the ribozyme-type (a) in which the genotype and the phenotype are carried on the same molecule is a simple system, success with RNA catalysts (ribozymes) has already been reported (Hiroshi Yanagawa (1993) New Age of RNA, pp.55–77, Yodosha).

Conceivable problem points of the cell-type (c) are (1) the averaging effect, (2) the eccentricity effect and (3) the random replication effect. The averaging effect arises because the assignment of the genotype to the phenotype statistically averages out and becomes ambiguous when the number of copies of the cell genome is large. Since an evolved genome is only one among the number of copies in a cell (n), performance enhancement averages out and a struggle for existence in the cell population begins at selection coefficient (s)/n. A smaller copy number (n) is therefore advantageous for the cell-type. Due to the presence of the eccentricity effect, however, when the number of segments is large, n must be very large to prevent the eccentricity effect. The apparent selection coefficient in the struggle for existence in the cell population can therefore be expected to be very much smaller than in the case of the virus-type. Since the time required for selection is proportional to the reciprocal of the selection coefficient, the rate of evolution is much slower than that of the virus-type. Further, the random replication effect (3) is fatal to the cell-type. This is because the random replication of segmented essential genes by this effect makes replication of all essential genes prior to cell division extremely difficult. This means that even if an essential gene with an advantageous mutation should occur, the probability of its being replicated and passed on to a daughter cell is extremely low.

Uniting of the genotype and the phenotype as in the virus-type (b) is necessary for efficient evolution.

Various techniques have already been proposed and are in the process of development for evolutionary molecular engineering of the virus-type (b) forming a complex of the genotype and the phenotype, including phage display (Smith, G. P. (1985) Science 228, 1315–1317; Scott, J. K. & Smith, G. P. (1990) Science 249, 386–390), polysome display (Mattheakis, L. C. et al. (1994) Proc. Natl. Acad. Sci. USA 91, 9022–9026), encoded combinatorial library (Brenner, S. & Lerner, R. A. (1992) Proc. Natl. Acad. Sci. USA 89, 5381–5383), and cellstat (Husimi, Y. et al. (1982) Rev. Sci. Instrum. 53, 517–522).

Despite the importance of the magnitude of the searchable sequence space in evolutionary molecular engineering, however, a method for globally searching a sequence space comparable to that of the ribozyme type has not yet been established for the virus-type.

The reason for this is that viruses currently used in the method such as phage displays are parasites of existing cells and are therefore unavoidably subject to restraints imposed by the host cells, among which can be listed: (1) that only a limited sequence space can be searched owing to restriction by the cells, (2) membrane permeability, (3) bias due to host, and (4) limitation on library owing to host population.

The polysome display method (Mattheakis, L. C. & Dower, W. J. (1995) WO95/11922) joins a nucleic acid and a protein via a ribosome by non-covalent bonding. It is therefore suitable when the chain length at the peptide position is short but encounters handling problems when the chain length is long as a protein. Since the huge ribosome remains interposed, the conditions at the time of the selection operation (e.g., adsorption, elution or the like) are subjected to severe restriction. The encoded combinatorial library (Janda, F. H. & Lerner, R. A. (1996) WO96/22391) assigns a chemically synthesized peptide to a nucleic acid tag via beads. Since the yield of chemical synthesis of proteins with around 100 residues is extremely poor using currently available technologies, however, this technique can be used with short chain-length peptides but not with long chain-length proteins.

One conceivable method of overcoming these problems is use of a cell-free translation system. A virus-type strategy molecule that simply binds the genotype and the phenotype in the cell-free systems has a number of advantages including the following: (1) that a huge mutant population approaching that of the ribozyme-type can be synthesized, (2) creation of various proteins without dependence on a host, (3) no problem regarding membrane permeability, and (4) that the 21st code can be used to introduce a non-native amino acid.

SUMMARY OF THE INVENTION

An object of the present invention is to provide a molecule comprising a virus-type operation replicon which has the advantages of the aforementioned virus-type strategy molecule, exhibits a higher efficiency than phages, and suffers fewer limitations concerning environmental condition setting, namely, a molecule which should be called "in vitro virus", wherein a nucleic acid and a protein are bound by a chemical bond, that is, a molecule in which a genotype is assigned to a phenotype. More specifically, the present invention has been accomplished in order to provide a molecule exhibiting one-on-one relationship between information and function, which can be utilized for creation of functional proteins and peptides, by performing genotype (nucleic acid) assignment to phenotype (protein) using a cell-free protein synthesis system, and binding the 3'-terminal end of a gene to the C-terminal end of a protein with a covalent bond on ribosome. Further, it is also an object of the present invention to obtain target functional proteins or peptides through investigation of vast sequence space, which is performed by repetition of selection of molecules that assign genotypes to phenotypes formed as described above (also referred to as "in vitro virus" hereinafter) by the in vitro selection method, and amplification of gene portions of the selected in vitro viruses by the reverse transcription PCR, and further amplification while introducing mutations.

The present inventors earnestly conducted investigations to achieve the aforementioned objects, and as a result, they found that two kinds of molecules that assign a genotype to a phenotype, comprising a nucleic acid and a protein which were chemically bound can be constructed on a ribosome in a cell-free protein synthesis system. They further found that a protein evolution simulation system can be constructed wherein the assigning molecules (in vitro viruses) were selected by the in vitro selection method, gene portions of the selected in vitro viruses were amplified by reverse transcription PCR, and the genes were further amplified while introducing mutations. The present invention has been accomplished based on these findings.

Thus, the present invention provides a molecule assigning a genotype to a phenotype, which comprises a nucleic acid portion having a nucleotide sequence reflecting the genotype, and a protein portion comprising a protein involved in exhibition of the phenotype, the nucleic acid portion and the protein portion being directly bound by a chemical bond.

According to preferred embodiments of the present invention, there are provided the aforementioned assigning molecule wherein a 3'-terminal end of the nucleic acid portion and a C-terminal end of the protein portion are bound by a covalent bond, and the aforementioned assigning molecule wherein a 3'-terminal end of the nucleic acid portion covalently bound to a C-terminal end of the protein portion is puromycin.

According to another preferred embodiment of the present invention, there is also provided the aforementioned assigning molecule wherein the nucleic acid portion comprises a gene encoding a protein, and the protein portion is a translation product of the gene of the nucleic acid portion. The nucleic acid portion preferably comprises a gene composed of RNA, and a suppressor tRNA bonded to the gene through a spacer. The suppressor tRNA preferably comprises an anticodon corresponding to a termination codon of the gene. Alternatively, the nucleic acid portion may comprise a gene composed of RNA, and a spacer portion composed of DNA and RNA, or DNA and polyethylene glycol. The nucleic acid portion may comprise a gene composed of DNA, and a spacer portion composed of DNA and RNA.

As further aspects of the present invention, there are provided a method for constructing a molecule assigning a genotype to a phenotype, which comprises (a) boding a DNA comprising a sequence corresponding to a suppressor tRNA, to a 3'-terminal end of a DNA containing a gene through a spacer, (b) transcribing the obtained DNA bonded product into RNA, (c) bonding, to a 3'-terminal end of the obtained RNA, a nucleoside or a substance having a chemical structure analogous to that of a nucleoside, which can be covalently bonded to an amino acid or a substance having a chemical structure analogous to that of an amino acid, and (d) performing protein synthesis in a cell-free protein synthesis system using the obtained bonded product as mRNA to bond a nucleic acid portion containing the gene to a translation product of the gene; and a method for constructing a molecule assigning a genotype to a phenotype, which comprises (a) preparing a DNA containing a gene which has no termination codon, (b) transcribing the prepared DNA into RNA, (c) bonding a chimeric spacer composed of DNA and RNA to a 3'-terminal end of the obtained RNA, (d) bonding, to a 3'-terminal end of the obtained bonded product, a nucleoside or a substance having a chemical structure analogous to that of a nucleoside, which can be covalently bonded to an amino acid or a substance having a chemical structure analogous to that of an amino acid, and (e) performing protein synthesis in a cell-free protein synthesis system using the obtained bonded product as mRNA to bond a nucleic acid portion containing the gene to a translation product of the gene.

According to a preferred embodiment of the present invention, there is provided the aforementioned construction method wherein the nucleoside or the substance having the chemical structure analogous to that of the nucleoside is puromycin.

As another aspect of the present invention, there is provided a method for constructing a molecule assigning a genotype to a phenotype, which comprises (a) preparing a DNA containing a gene which has no termination codon, (b) transcribing the prepared DNA into RNA, (c) bonding a chimeric spacer composed of DNA and polyethylene glycol to a 3'-terminal end of the obtained RNA, (d) bonding, to a 3'-terminal end of the obtained bonded product, a nucleoside or a substance having a chemical structure analogous to that of a nucleoside, which can be covalently bound to an amino acid or a substance having a chemical structure analogous to that of an amino acid, and (e) performing protein synthesis in a cell-free protein synthesis system using the obtained bonded product as mRNA to bond a nucleic acid portion containing the gene to a translation product of the gene.

As another aspect of the present invention, there is provided a method for constructing a molecule assigning a genotype to a phenotype, which comprises (a) preparing a DNA containing a gene which has no termination codon, (b) transcribing the prepared DNA into RNA, (c) bonding a spacer composed of double-stranded DNA to a 3'-terminal end of the obtained RNA, (d) bonding, to a 3'-terminal end of the obtained bonded product, a nucleoside or a substance having a chemical structure analogous to that of a nucleoside, which can be covalently bound to an amino acid or a substance having a chemical structure analogous to that of an amino acid, and (e) performing protein synthesis in a cell-free protein synthesis system using the obtained bonded product as mRNA to bond a nucleic acid portion containing the gene to a translation product of the gene.

As a further aspect of the present invention, there is provided a method for constructing a molecule assigning a genotype to a phenotype, which comprises (a) preparing a DNA containing a gene which has no a termination codon, and a nucleotide sequence of a spacer, (b) transcribing the prepared DNA into RNA, (c) bonding, to a 3'-terminal end of the obtained RNA, a nucleoside or a substance having a chemical structure analogous to that of a nucleoside, which can be covalently bonded to an amino acid or a substance having a chemical structure analogous to that of an amino acid, (d) adding a short chain PNA or DNA to a 3'-terminal end side portion of the gene in the obtained RNA bonded product to form a double-stranded chain, and (e) performing protein synthesis in a cell-free protein synthesis system using the obtained bonded product as mRNA to bond a nucleic acid portion containing the gene to a translation product of the gene.

As a still further aspect of the present invention, there is provided a method for protein evolution simulation, which comprises a construction step for constructing assigning molecules from a DNA containing a gene by any one of the construction methods mentioned above, a selection step for selecting the assigning molecules obtained in the construction step, a mutation introduction step for introducing a mutation into a gene portion of an assigning molecule selected in the selection step, and an amplification step for amplifying the gene portion obtained in the mutation introduction step. In the method for evolution simulation, the construction step, the selection step, the mutation introduction step and the amplification step are preferably performed repeatedly by providing the DNA obtained in the amplification step to the construction step. Further, there is provided an apparatus for performing the aforementioned method for evolution simulation, which comprises a means for constructing assigning molecules, said means comprising a first bonding means for bonding a DNA comprising a sequence corresponding to a suppressor tRNA to a 3'-terminal end of a DNA containing a gene through a spacer, a transcription means for transcribing the DNA bonded product obtained by the first bonding means into RNA, a second bonding means for bonding, to a 3'-terminal end of the RNA obtained by a transcription means, a nucleoside or a substance having a chemical structure analogous to that of a nucleoside, which can be covalently bound to an amino acid or a substance having a chemical structure analogous to that of an amino acid, and a third bonding means for performing protein synthesis in a cell-free protein synthesis system using the bonded product obtained by the second bonding means as mRNA to bond a nucleic acid portion containing the gene to a translation product of the gene, or a means for constructing assigning molecules, said means comprising a transcription means for transcribing a DNA containing a gene into RNA, a first bonding means for bonding a chimeric spacer composed of DNA and RNA, a chimeric spacer composed of DNA and polyethylene glycol, a double-stranded spacer composed of DNA and DNA, or a double-stranded spacer composed of RNA and a short chain peptide nucleic acid (PNA) or DNA to a 3'-terminal end of the RNA obtained by the transcription means, a second bonding means for bonding, to a 3'-terminal end of the RNA-spacer bonded obtained by the first bonding means, a nucleoside or a substance having a chemical structure analogous to that of a nucleoside, which can be covalently bound to an amino acid or a substance having a chemical structure analogous to that of an amino acid, and a third bonding means for performing protein synthesis in a cell-free protein synthesis system using the bonded product obtained by the second bonding means as mRNA to bond a nucleic acid portion containing the gene to a translation product of the gene; a selection means for selecting the constructed assigning molecules; a mutation introduction means for introducing a mutation into a gene portion of an assigning molecule selected; and an amplification means for amplifying the gene portion to which the mutation is introduced.

As a still further aspect of the present invention, there is provided a method for assaying protein/protein or protein/nucleic acid intermolecular action, which comprises a construction step for constructing assigning molecules by any one of the aforementioned construction methods, and an assay step for examining intermolecular action of the assigning molecules obtained in the construction step with another protein or nucleic acid.

DESCRIPTION OF THE PREFERRED EMBODIMENTS

Figure 1:
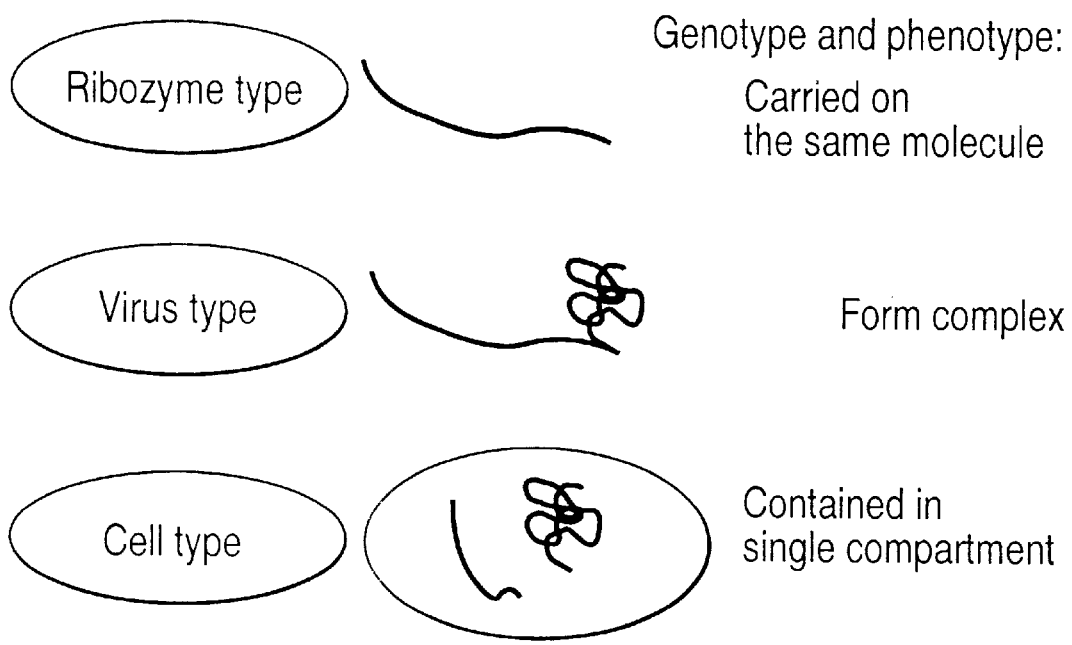
FIG. 1 shows strategies for genotype (nucleic acid portion) assignment to phenotype (protein portion).

In this specification, some technical terms are used, and those technical terms have the following meanings when herein used. The term "nucleic acid portion" means a bonded product of a nucleoside or a substance having a chemical structure analogous to a nucleoside, for example, RNA, DNA, PNA (peptide nucleic acid; polymers comprising nucleic acids linked via amino acid analogues) and the like, and "protein portion" means a bonded product of an amino acid or a substance having a chemical structure analogous to an amino acid such as naturally-occurring amino acids and non-naturally-occurring amino acids. The term "suppressor tRNA (sup tRNA)" means a tRNA which can suppress mutation by structural change, for example, reading a termination codon on mRNA as a codon corresponding to a certain amino acid. The expression of "having a nucleotide sequence reflecting genotype" means to contain a gene or a part thereof relating to a genotype. The expression of "containing a protein involved in exhibition of phenotype" means to contain, for example, a protein whose expression itself is a characteristic of phenotype, a protein involved in exhibition of a characteristic of phenotype by its function as an enzyme or the like.

The spacer located at the 3'-terminal end side of the nucleic acid portion may be any spacer provided that it is a polymer substance preferably having a length of not less than 100 Å, more preferably about 100 to 1000 Å. Specifically, single-stranded chains of RNA or DNA, double-stranded chains of DNA and DNA, double-stranded chains of RNA and short chain PNA or DNA (e.g., about 15 to 25 nucleotides), and polymer materials such as polysaccharides, which are naturally-occurring or synthetic, synthetic organic polymer substances such as polyethylene glycols, preferably polyethylene glycols having a molecular weight of about 3,000 to 30,000 and the like can be mentioned.

The nucleic acid portion and the protein portion of the assigning molecule of the present invention are linked through a chemical bond such as a covalent bond. In particular, preferred are those formed by bonding a nucleoside or a substance having a chemical structure analogous to a nucleoside, or a linked product thereof present at the 3'-terminal end of the nucleic acid portion to an amino acid or a substance having a chemical structure analogous to an amino acid present at the C-terminal end of the protein portion via a chemical bond, for example, a covalent bond.

For the bonding between the nucleic acid portion and the protein portion, for example, puromycin, 3'-N-aminoacylpuromycin aminonucleoside (PANS-amino acid), which have an amide bond as the chemical bond at the 3'-terminal end of the nucleic acid portion, e.g., PANS-Gly wherein the amino acid portion is glycine, PANS-Val wherein the amino acid portion is valine, PANS-Ala wherein the amino acid portion is alanine, and further PANS-(any of the other amino acids) wherein the amino acid portion is an of the other amino acids, can be utilized. 3'-N-Aminoacyl-adenosine aminonucleoside (AANS-amino acid), which comprises as the chemical bond an amide bond formed by dehydration condensation of the amino group of 3'-aminoadenosine and the carboxyl group of an amino acid, for example, AANS-Gly wherein the amino acid portion is glycine, AANS-Val wherein the amino acid portion is valine, AANS-Ala wherein the amino acid portion is alanine, and further AANS-(any of the other amino acids) wherein the amino acid portion is any of the other amino acids, can also be utilized. Those composed of a nucleoside or a nucleoside bound to an amino acid via an ester bond may also be used. Further, any other materials having a binding mode capable of binding a nucleoside or a substance having a chemical structure analogous to a nucleoside and an amino acid or a substance having a chemical structure analogous to an amino acid can also be utilized.

The molecule assigning the genotype to the phenotype of the present invention can be constructed by, for example, (1) a method where the binding of the nucleic acid portion and the protein portion is formed in a site-directed manner, or (2) a method where the bonding of the nucleic acid portion and the protein portion is formed in a non-site-directed manner, which will be explained hereinafter.

First, (1) the method where the bonding of the nucleic acid portion and the protein portion is formed in a site-directed manner will be explained.

In this method, a molecule assigning a genotype to a phenotype can be constructed by (a) bonding a DNA comprising a sequence corresponding to sup tRNA, to the 3'-terminal end of a DNA containing a gene through a spacer, (b) transcribing the obtained DNA bonded product into RNA, (c) bonding, to the 3'-terminal end of the obtained RNA, a nucleoside or a substance having a chemical structure analogous to that of a nucleoside, which can be covalently bound to an amino acid or a substance having a chemical structure analogous to that of an amino acid, e.g., puromycin, (d) performing protein synthesis in a cell-free protein synthesis system, e.g., an E. coli cell-free protein synthesis system, using the obtained bonded product as mRNA, and thus (e) affording a molecule assigning a genotype to a phenotype comprising a gene RNA (genotype) and a protein (phenotype) which is a translation product of the gene, which are chemically bound through a nucleoside or a substance having a chemical structure analogous to that of a nucleoside, e.g., puromycin.

Figure 2:
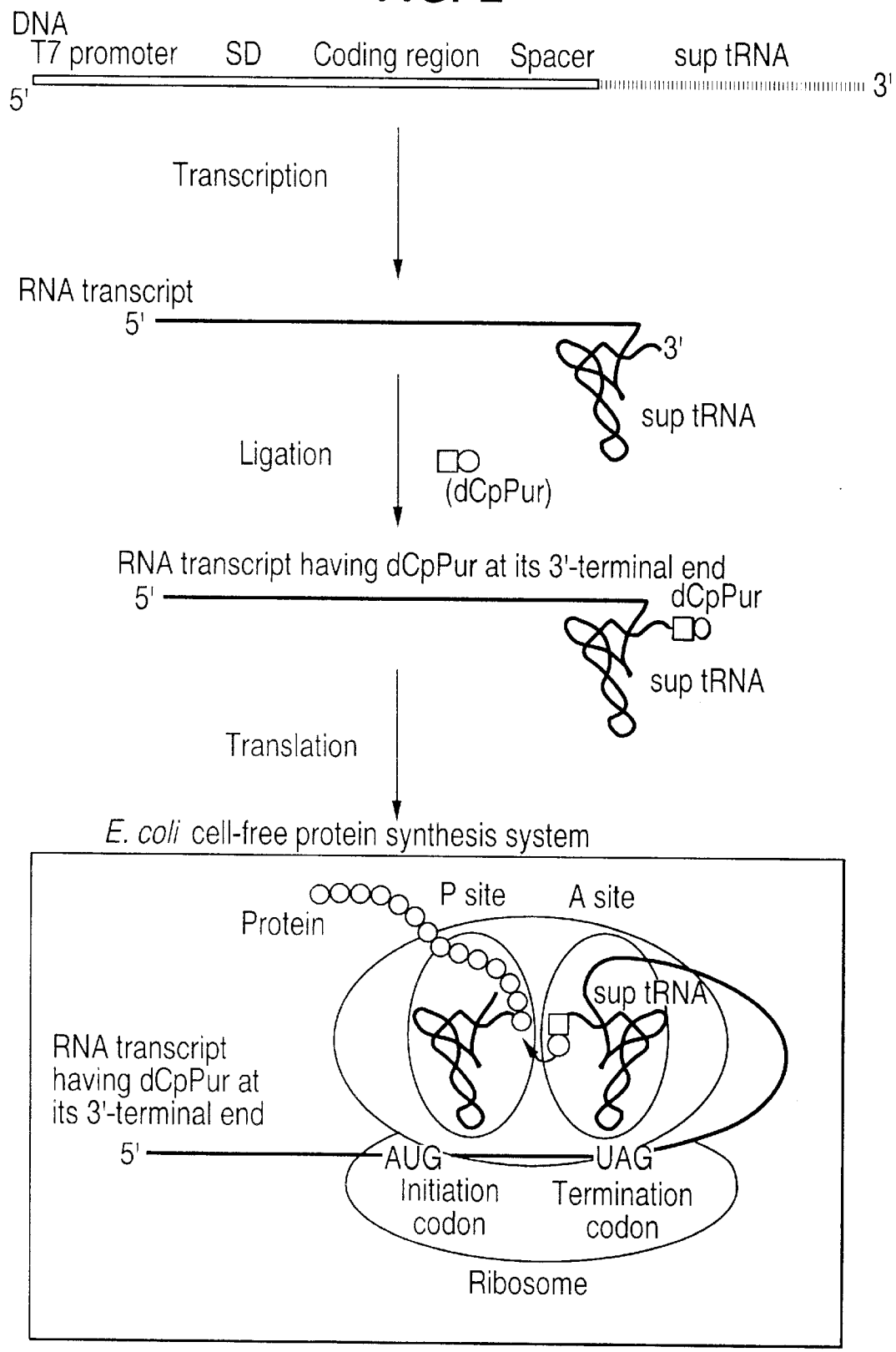
FIG. 2 shows a method for construction of the molecule assigning the genotype to the phenotype of the present invention wherein a nucleic acid portion and a protein portion are bonded in a site-directed manner.

That is, according to this method of the present invention, when a termination codon comes into the A site of ribosome during the protein synthesis, a sup tRNA is correspondingly incorporated, and a nucleoside or a substance having a chemical structure analogous to that of a nucleoside, e.g., puromycin, present at the 3'-terminal end of the sup tRNA is bound to a protein by the action of peptidyl transferase (FIG. 2). Therefore, this method is site-directed as for the formation of the bonding between the nucleic acid portion and the protein, which depends on the genetic code.

Figure 3:
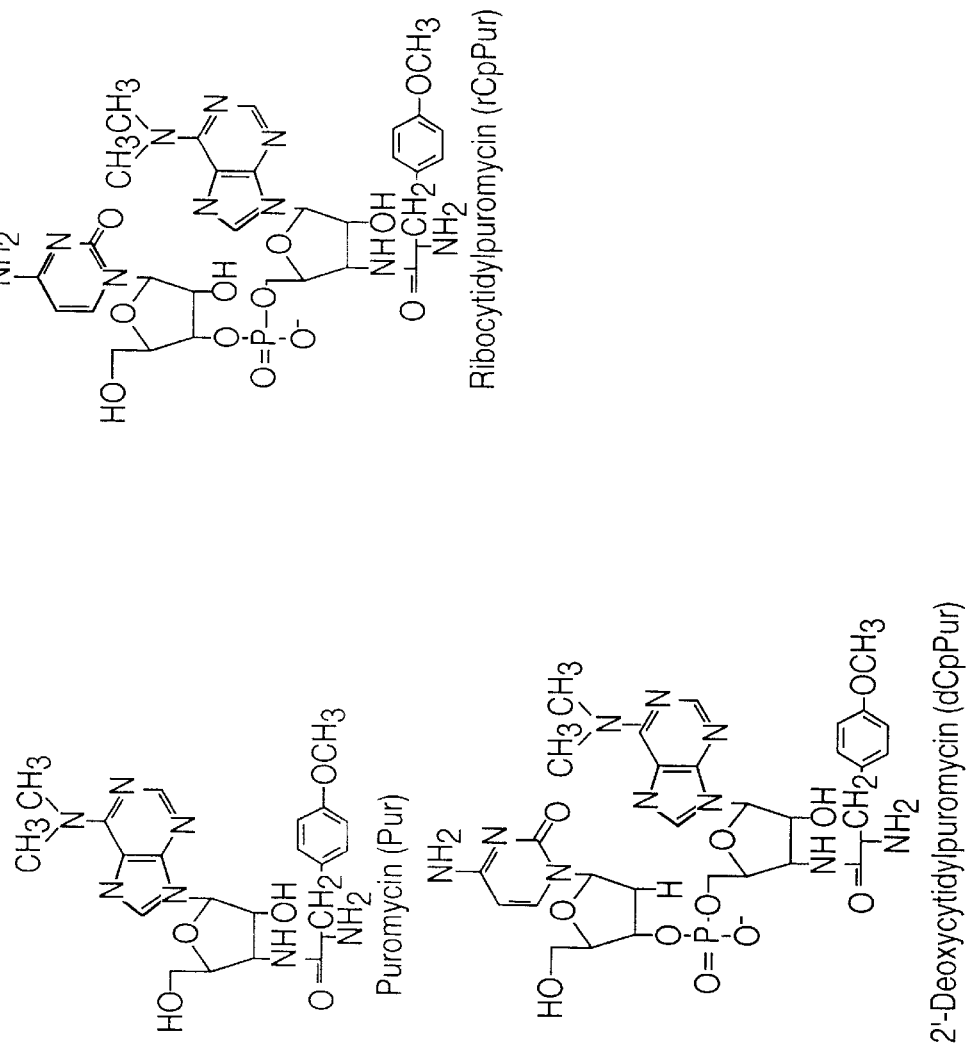
FIG. 3 shows chemically-modified portions of the 3'-terminal ends of nucleic acid portions, which are a point of the construction of the molecule assigning the genotype to the phenotype (in vitro virus).

It has been known that puromycin (FIG. 3) inhibits the protein synthesis in bacteria (Nathans, D. (19.64) Proc. Natl. Acad. Sci. USA, 51, 585–592; Takeda, Y. et al. (1960) J. Biochem. 48, 169–177) and animal cells (Ferguson, J. J. (1962) Biochim. Biophys. Acta 57, 616–617; Nemeth, A. M. & de la Haba, G. L. (1962) J. Biol. Chem. 237, 1190–1193). Puromycin, whose structure resembles the structure of aminoacyl tRNA, reacts with peptidyl tRNA bound to the P site of ribosome, and it is released from ribosome as peptidyl puromycin, and thus interrupts the protein synthesis (Harris, R. J. (1971) Biochim. Biophys. Acta 240, 244–262).

It is not practical to purify native sup tRNA and bond it to mRNA, because of the problems concerning the purification of sup tRNA and the easily hydrolyzable ester bond at the 3'-terminal end of tRNA. Through investigations of tRNA identity, it has been elucidated that unmodified tRNA may be aminoacylated like intact tRNA, and that the aminoacylated unmodified tRNA may be taken into ribosome, and translated (Shimizu, M. et al. (1992) J. Mol. Evol. 35, 436–443). The identity of tRNA is also utilized in order to prepare sup tRNA.

It has been reported that the aminoacyl synthetases of alanine, histidine, and leucine do not recognize the anticodons thereof (Tamura, K. et al. (1991) J. Mol. Recog. 4, 129–132). Therefore, it can be expected that, by replacing the anticodon of tRNA for alanine with a termination codon (e.g., amber), tRNA for alanine (sup tRNA) would be incorporated corresponding to the termination codon.

In this respect, it comes into question whether tRNA whose 5'-terminal-end side is not made up by RNAse P or the like, unlike ordinary tRNA, may enter into the A site of ribosome or not. This is the most important problem to be investigated in determining feasibility of the model of the present invention. It has been known that the 3'-terminal ends of Brome Mosaic Virus (BMV) and Turnip Yellow Mosaic Virus (TYMV) have a tRNA-like structure, and they are aminoacylated by aminoacyl synthetase, and incorporated at an efficiency of 1% in a cell-free translation system (Chen, J. M. & Hall, T. C. (1973) Biochemistry 12, 4570–4574). Supposing that RNA of BMV is incorporated even by 1% by ribosome, it can be expected that RNA having intact tRNA at its 3'-terminal end may be incorporated more efficiently. Even if it is incorporated at an efficiency of 10% or less of that of intact tRNA, there is a reasonable possibility that it can win the competition with the release factor by the concentration effect.

Therefore, before the experiment for bonding a protein to the 3'-terminal end of mRNA-sup tRNA (MRNA ligated at its 3'-terminal end with sup tRNA through a spacer), it was examined whether even sup tRNA separated from mRNA entered into the A site of ribosome and was bound to a protein. A sup tRNA whose 3'-terminal end was bonded to puromycin was actually prepared, and added to a cell-free protein synthesis system to examine whether the sup tRNA portion entered into the A site of ribosome corresponding to occurrence of a termination codon and bound to a protein. The 4 repeats region of tau protein (127 residues) was used as mRNA (Goedert, M. (1989) EMBO J. 8,392–399). As a result, when the translation was performed in a cell-free protein synthesis system, it could be confirmed that the sup tRNA having puromycin at its 3'-terminal end was incorporated into the A site of ribosome corresponding to a termination codon and bound to a protein (FIG. 2).

Then, RNA-sup tRNA bonded products having different lengths of the spacer between mRNA and sup tRNA were constructed, and it was attempted to select an optimum length of the spacer which afforded the best efficiency of the incorporation of the sup tRNA portion into the A site of ribosome by the in vitro selection method. As a result, it was found that the RNA-sup tRNA bonded product having a certain spacer length was chemically bound to a protein that was a translation product thereof with a good efficiency.

In order to construct the molecule assigning the genotype to the phenotype of the present invention, a nucleoside or a substance having a chemical structure analogous to that of a nucleoside, which is to be bonded to the 3'-terminal end of the nucleic acid portion, and can be covalently bound to an amino acid or a substance having a chemical structure analogous to that of an amino acid, e.g., 2'-deoxycytidylylpuromycin (dCpPur) and ribocytidylpuromycin (rCpPur) (FIG. 3), must be synthesized first.

An exemplary method for synthesizing dCpPur is as follows. First, puromycin-5'-monophosphate can be prepared by chemically phosphorylating the 5'-hydroxyl group of puromycin using phosphorus oxychloride and trimethylphosphate. Then, the amino group of the amino acid portion and the 2'-hydroxyl group of the ribose portion in puromycin-5'-monophosphate can be protected by reacting puromycin-5'-monophosphate with trifluoroacetic acid and trifluoroacetic anhydride. The protected product can be reacted with Bz-DMT deoxycytidine in which the amino group of the pyrimidine ring and the 5'-hydroxyl group of the ribose portion in deoxycytidine are protected, in the presence of a condensation agent, dicyclohexylcarbodiimide, and then deprotected with acetic acid and ammonia to afford 2'-deoxycytidylylpuromycin (dCpPur). pdCpPur can be obtained by phosphorylating the 5'-hydroxyl group of dCpPur with polynucleotide kinase.

The ribocytidylpuromycin can be prepared by condensing puromycin and rC-β-amidite having protective groups in the presence of tetrazole, and oxidizing and deprotecting the product.

Then, the construction of a bonded product constituting the nucleic acid portion for binding the nucleic acid portion and the protein portion in a site-directed manner will be described hereinafter.

As the bonded product constituting the nucleic acid portion used for the site-directed method, for example, a bonded product comprising 5'-(T7 promoter region)-(Shine-Dalgarno (SD) sequence region)-(mRNA region)-(spacer region)-(sup tRNA region)-(puromycin region)-3' connected in this order in sequence can be mentioned.

In the construction of this bonded product for the nucleic acid portion, a plasmid comprising the 4 repeats region, which is a microtuble-binding region of human tau protein called htau24 (Goedert, M. (1989) EMBO J. 8, 392–399), inserted downstream of T7 promoter (pAR3040) is constructed first, and it is digested with restriction enzymes BglII and BamHI to afford a linear DNA. This DNA is used as a template, and amplification is carried out by PCR by using primers for upstream region containing T7 region (forward) and for downstream region containing the SD region and a region around the initiation codon (backward), and Taq DNA polymerase.

In the above method, three methionines may be added to the backward primer in order to enhance detection sensitivity for radioactive methionine in the protein portion after the protein synthesis. That is, leucine at position 4, and lysines at positions 5 and 8 of the 4 repeats region are replaced with methionines. Eventually, the translated 4 repeats protein contains four methionines in total. Then, amplification is carried out by PCR using a DNA containing the aforementioned linearized 4 repeats region as a template, a complementary chain of the, backward primer mentioned above as a forward primer, and a backward primer which is designed so that the C-terminal end of the 4 repeats region should have an amber codon as the termination codon.

The two kinds of DNA fragments amplified by the PCR, namely, the DNA fragment containing the T7 promoter and the SD region and the DNA fragment containing the 4 repeats region are mixed, initially extended without primers, and then amplified by PCR again by using a primer containing the sequence of T7 promoter as the forward primer, and a primer containing a termination codon at the C-terminal of the 4 repeats region as the backward primer.

This DNA bonded product (T7 promoter-SD-4 repeats) is ligated to a double-stranded DNA fragment having cohesive ends at the both ends and composed of 17 residues in tandem by using DNA ligase to afford ligation products having different spacer lengths.

After the ligation, the product was fractionated into three fractions (a, b, c) based on the length by polyacrylamide gel electrophoresis (PAGE). The spacer is represented as (17)n wherein n=15 to 18 for the fraction a, n=6 to 14 for the fraction b, and n=0 to 5 for the fraction c. As the sup tRNA, a native alanyl tRNA whose several sites and anticodon are modified into amber (UAG) is prepared by chemical synthesis. This sup tRNA is ligated to the ligation products of the fractions a, b and c having different spacer lengths by using T4 DNA ligase. For the ligation site, an excessive amount of a single-stranded backing DNA is used, and after once melted by temperature elevation, the strands are annealed, and a complementary strand is formed, and ligated. After the ligation, the ligation product is amplified by PCR using primers for the 5' end and 3'-terminal end of the ligation product. This DNA ligation product is transcribed by using T7 RNA polymerase to form an RNA ligation product.

By ligating the pdCpPur chemically synthesized in the above to the 3w-terminal end of this RNA ligation product using T4 RNA ligase, there can be obtained an RNA ligation product, 5'-(T7 promoter region)-(SD region)-(4 repeats region)-(spacer region)-(sup tRNA region)-(puromycin)-3', which can be used as a gene in a cell-free protein synthesis system.

The protein synthesis is performed by adding the above RNA ligation product as mRNA to a cell-free protein synthesis system such as cell-free protein synthesis extracts of E. coli or rabbit reticulocytes. In order to obtain an optimum spacer length for obtaining the most efficient bonding of the nucleic acid portion (RNA) and the protein portion, the following experiment is performed.

That is, the protein synthesis is performed in a cell-free protein synthesis system by using aforementioned RNA ligation products having three kinds of different spacer lengths, corresponding to the fractions a, b and c, as the gene. In this synthesis, by adding tRNA charged with modified lysine comprising biotin bound through the ε-amino group of the lysine, biotinyllysine is incorporated in several positions of lysine residues in the translated 4 repeats protein. After the protein synthesis, magnetic beads coated with streptavidin on their surfaces are added to isolate the protein incorporating the biotin.

If the nucleic acid portion (RNA) has bonded to the protein portion through puromycin, the nucleic acid portion (RNA) should be bound to the C-terminal end of the protein. When reverse transcription was performed by using a sequence corresponding to the N-terminal region of the 4 repeats as a forward primer and the 3'-terminal end portion of sup tRNA as a backward primer and analyzed by polyacrylamide gel electrophoresis to confirm whether the RNA-protein-bonded product was actually picked up by the magnetic beads, a band of reverse transcribed DNA was observed only for the spacer length of the fraction c. This means that the RNA ligation product having the spacer length of the fraction c is most efficiently bound to the protein portion.

Now, it will be explained about (2) the method where the bonding of the nucleic acid portion and the protein portion is formed in a non-site-directed manner.

In this method, a molecule assigning a genotype to a phenotype can be constructed by (a) preparing a DNA containing a gene which has no termination codon, (b) transcribing the prepared DNA into RNA, (c) bonding a chimeric spacer composed of DNA and RNA to the 3'-terminal end of the obtained RNA, (d) bonding, to the 3'-terminal end of the bonded product, a nucleoside or a substance having a chemical structure analogous to that of a nucleoside, which can be covalently bound to an amino acid or a substance having a chemical structure analogous to that of an amino acid, e.g., puromycin, (e) performing protein synthesis in a cell-free protein synthesis system using the obtained bonded product as mRNA, and thus (f) affording a molecule assigning a genotype to a phenotype comprising a gene RNA and a protein which is a translation product of the gene, which are chemically bound through puromycin or the like.

Figure 4:
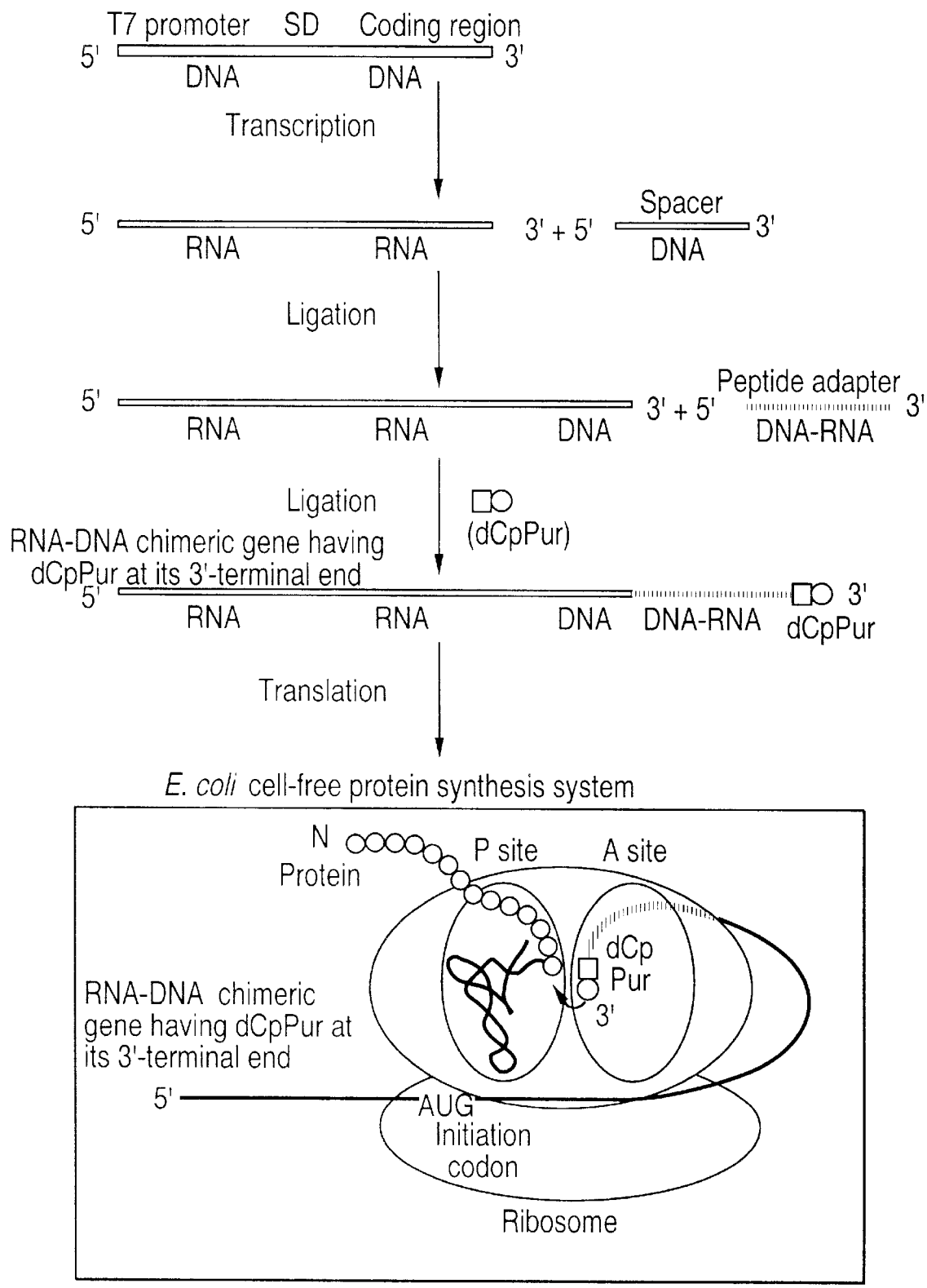
FIG. 4 shows a method for construction of the molecule assigning the genotype to the phenotype of the present invention wherein a nucleic acid portion and a protein portion are bonded in a non-site-directed manner.

That is, according to this method of the present invention, a nucleoside or a substance having a chemical structure analogous to that of a nucleoside, e.g., puromycin, present at the 3'-terminal end of the nucleic acid portion does not enter into the A site of ribosome corresponding to the termination codon of mRNA on ribosome, but randomly enters depending on the spacer length, and puromycin or the like at the 3'-terminal end of the RNA-DNA chimera nucleic acid portion is chemically bound to a protein by the action of peptidyl transferase (FIG. 4). Therefore, this method is non-site-directed as for the formation of the bonding between the nucleic acid portion and the protein, which does not depend on the genetic code.

In this method, the molecule assigning the genotype to the phenotype can be constructed by using a non-site-directed ligation product for the nucleic acid portion in the same manner as in the aforementioned site-directed method of (1).

As the ligation product constituting the nucleic acid portion used for the non-site-directed method, for example, a ligation product composed of 5'-(T7 promoter region)-(Shine-Dalgarno (SD) sequence region)-(mRNA region)-(spacer region)-(puromycin region)-3' connected in this order in sequence can be mentioned.

In the construction of this ligation product for the nucleic acid portion, the construction from the T7 promoter region to the end of the 4 repeats region may be similar to that explained for the construction of the ligation product for the nucleic acid portion used in (1) the site directed method mentioned above, provided that a primer designed not to have a termination codon by replacing the two termination codons at the C-terminal end of the 4 repeats, ochre (CTG) and amber (TAA), with CAG (glutamine) and AAA (lysine), respectively, is used as a backward primer for the PCR amplification of the ligation product constructed above used as a template.

This DNA ligation product is transcribed as a template by using T7 RNA polymerase to afford a corresponding RNA ligation product. This single-stranded RNA ligation product is separately ligated to each of single-stranded chemically-synthesized DNA linkers (chain length; 20, 40, 60, and 80 nucleotides) by using T4 RNA ligase. Then, each ligation product is ligated to a single-stranded DNA-RNA chimeric oligonucleotide comprising 25 residues (DNA; 21 residues, RNA; 4 residues), which is designated as peptide acceptor, by using T4 DNA ligase in the presence of a single-stranded backing DNA.

Because the sequence of the peptide acceptor contains the 3'-terminal end sequence of alanyl tRNA, and it enhances the incorporation of a puromycin derivative into the A site of ribosome, it is preferable to use the peptide acceptor between the spacer region and the puromycin region.

By ligating the pdCpPur chemically synthesized in the above to the 3'-terminal end of the above ligation product using T4 RNA ligase, there can be obtained an RNA-DNA chimeric ligation product, 5'-(T7 promoter region (RNA))-(SD region (RNA))-(4 repeats region (RNA))-(spacer region (DNA))-(peptide acceptor region)-(puromycin)-3', which can be used as a gene for a cell-free protein synthesis system.

If protein synthesis is performed by using the RNA-DNA chimeric ligation product mentioned above as a gene in a cell-free protein synthesis system, there can be obtained a bonded product comprising a nucleic acid portion (RNA-DNA chimeric ligation product, genotype) and a protein portion (phenotype), which are connected by a chemical bond through puromycin.

In the aforementioned method, a chimeric spacer of DNA and polyethylene glycol can also be used instead of the chimeric spacer of DNA and RNA.

In the above method, a spacer composed of a double-stranded chain of DNA and DNA, or a double-stranded chain of RNA and short chain PNA or DNA (e.g., about 15 to 25 nucleotides) may also be used instead of the chimeric spacer of DNA and RNA. The spacer composed of the double strand of DNA and DNA is not necessary to be double-stranded in its full length, and it may be double-stranded for most part (usually, several residues at the both ends are single-stranded, and remaining portion is double-stranded). The double-stranded spacer composed of RNA and short chain PNA or DNA can also be prepared by (a) preparing a DNA containing a gene which has no termination codon, and a nucleotide sequence of a spacer, (b) transcribing the prepared DNA into RNA, (c) bonding, to the 3'-terminal end of the obtained RNA, a nucleoside or a substance having a chemical structure analogous to that of a nucleoside, which can be covalently bound to an amino acid or a substance having a chemical structure analogous to that of an amino acid, and (d) adding a short chain PNA or DNA to a 3'-terminal-end side portion of the gene in the obtained RNA bonded product to form a double-stranded chain.

The genetic engineering techniques mentioned in the present specification such as isolation and preparation of nucleic acids, ligation of nucleic acids, synthesis of nucleic acids, PCR, construction of plasmids, and translation in cell-free system can be performed by the methods described in Sambrook et al. (1989) Molecular Cloning, 2nd Edition, Cold Spring Harbor Laboratory Press, or similar methods unless otherwise indicated.

The assigning molecule of the present invention can also be obtained by successively bonding each of the elements by any known chemical bonding methods in addition to the methods exemplified above.

Figure 12:
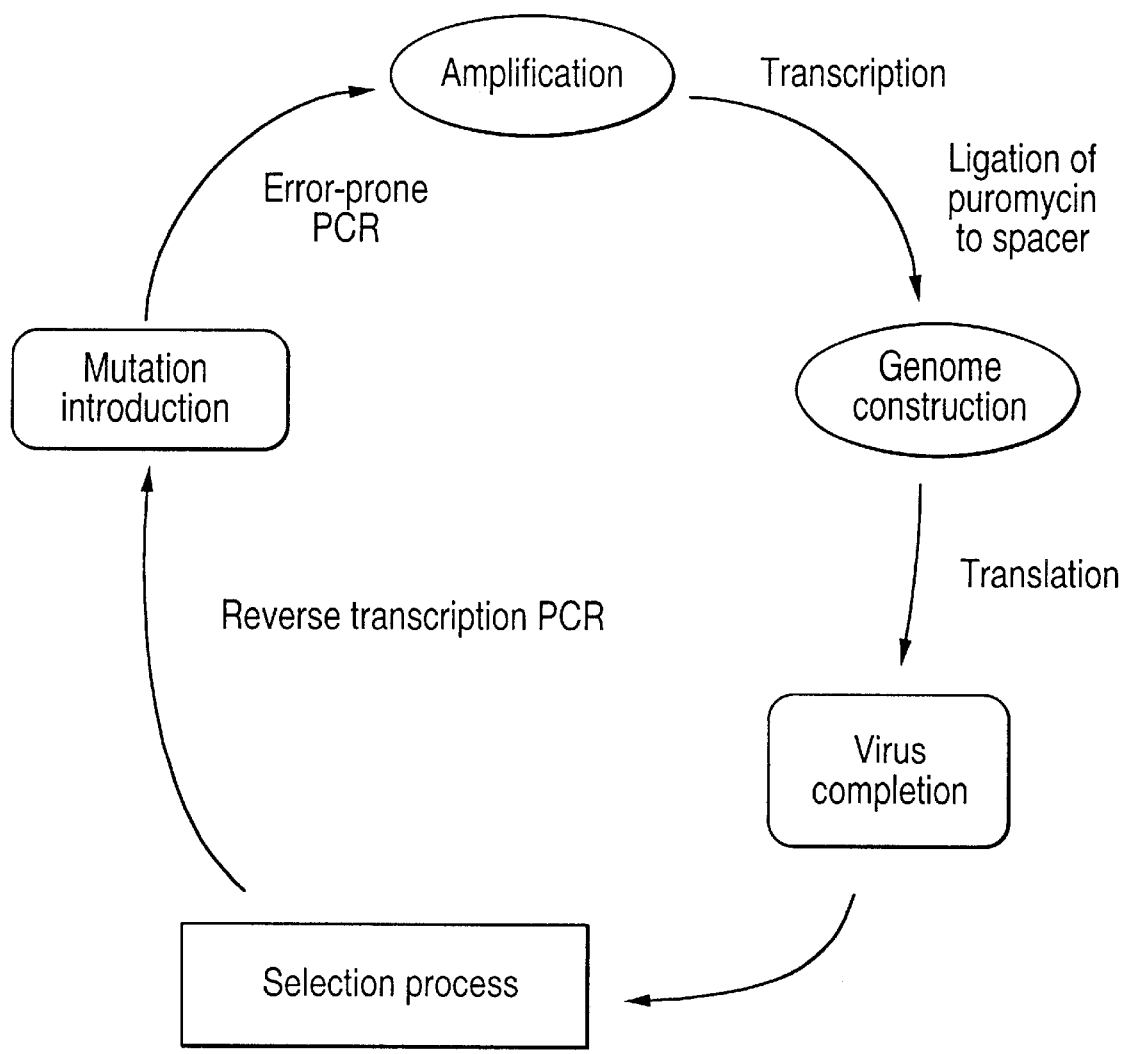
FIG. 12 shows process steps of a protein evolution simulation method utilizing in vitro viruses.

The protein evolution simulation method of the present invention is a method comprising steps of (1) construction of in vitro virus genomes, (2) completion of in vitro viruses, (3) selection process, (4) introduction of mutation, and (5) amplification, as shown in FIG. 12. These steps or repetition of these steps as required allows modification and creation of functional proteins. Among these steps, the steps of (1) and (2) can be performed by the construction methods explained above in detail. That is, the step (1) corresponds to construction of the bonded product comprising the nucleoside or the substance having the chemical structure analogous to that of the nucleoside, and the step (2) corresponds to the construction of the assigning molecule from the bonded product. The steps of (3), (4) and (5) will be described hereinafter.

The selection process of (3) means a process of evaluating function (biological activity) of protein portions constituting the in vitro viruses, and selecting in vitro viruses based on a desired biological activity. Such a process has been known, and described in, for example, Scott, J. K. & Smith, G. P. (1990) Science, 249, 386–390; Devlin, P. E. et al. (1990) Science, 249, 404–406; Mattheakis, L. C. et al. (1994) Proc. Natl. Acad. Sci. USA, 91, 9022–9026 and the like.

Then, mutations are introduced into the nucleic acid portions of the selected in vitro viruses, and the in vitro viruses are amplified by PCR or the like in the steps of (4) introduction of mutation, and (5) amplification. When the nucleic acid portion of in vitro viruses is composed of RNA, mutation can be introduced after a cDNA is synthesized by reverse transcriptase. The amplification of the nucleic acid portion may also be performed while introducing mutation. The introduction of mutation can be readily performed by already established error-prone PCR (Leung, D. W., et al., (1989) J. Methods Cell Mol. Biol., 1, 11–15), Sexual PCR (Stemmer, W. P. C. (1994) Proc. Natl. Acad. Sci. USA 91, 10747–10751) or the like.

(1) In vitro virus genomes can be constructed by using nucleic acid portions for in vitro viruses which have been introduced with mutation and amplified, (2) in vitro viruses can be completed by using the in vitro virus genomes, (3) in vitro viruses can be selected based on a desired biological activity, and (4) mutation introduction and amplification can be carried out. By repeating these steps as required, modification and creation of functional proteins can be realized.

The means contained in the apparatus of the present invention for performing the aforementioned protein evolution simulation method themselves are known ones, and operations in these means such as addition of reagents, stirring, temperature control, and evaluation of biological activity can be performed according to the methods known per se. By combining these operations, an automatic or semi-automatic apparatus of the present invention can be constructed.

The step of constructing assigning molecules in the method for assaying protein/protein or protein/nucleic acid intermolecular action of the present invention generally comprises steps of (1) synthesizing mRNA from a gene library or a cDNA library, and constructing an in vitro genome, and (2) constructing an in vitro virus comprising mRNA and a corresponding protein, which are bonded on ribosome, by utilizing a cell-free protein synthesis system.

The step (1) corresponds to synthesis of mRNA using RNA polymerase from cDNA of DNA of which sequence has been known and which contains a sequence corresponding to ORF, cDNA of DNA of which sequence is unknown and which contains a fragment resulting from fragmentation with a suitable restriction enzyme or the like, and construction of an in vitro virus genome by utilizing the mRNA.

The steps of above (1) in vitro virus genome construction, and (2) in vitro virus construction can be performed by the construction methods explained above in detail.

The assay step for examining intermolecular action between assigning molecules and other proteins or nucleic acids (DNA or RNA) usually comprises steps of (3) selecting only proteins having a particular function from the in vitro viruses constructed in the step (2), and (4) subjecting selected in vitro viruses to reverse transcription, amplification, and sequencing.

In the step (3), target proteins or nucleic acids (DNA or RNA) and other substances, for example, saccharides and -lipids, are bound to a microplate, beads or the like beforehand through covalent bonds or non-covalent bonds, and the in vitro viruses constructed in the step (2) are added thereto, to react under a certain temperature condition for a certain period of time, and it is washed to remove in vitro viruses which has not been bound to the target. Then, the in vitro viruses which have been bound to the target are released. This step can be performed by the already-established ELISA (Enzyme Linked Immunosorbent Assay, Crowther, J. R. (1995) Methods in Molecular Biology, Vol. 42, Humana Press Inc.) or a similar technique.

In the step (4), the in vitro viruses released in the step (3) are reverse-transcribed and amplified by reverse transcription PCR, and the amplified DNA was sequenced directly or after cloning.

According to the assay method of the present invention, it becomes possible to identify a function of a gene product (protein) corresponding to a gene whose function is unknown by (1) synthesizing mRNA from gene DNA whose sequence is known or unknown to construct in vitro virus genomes, (2) constructing in vitro viruses by using the in vitro virus genomes, (3) selecting only those binding to a target protein or nucleic acid or other substances, for example, saccharides and lipids from among the in vitro viruses, and (4) subjecting selected in vitro viruses to reverse transcription, amplification, cloning and sequencing.

To perform the method for assaying intermolecular action mentioned above, an apparatus can be constructed by combining known appropriate means. The means contained in the apparatus may be per se known ones, and operations in these means such as addition of reagents, stirring, temperature control, and evaluation of biological activity can be performed according to the methods known per se. By combining these operations, an automatic or semi-automatic apparatus for assaying intermolecular action can be constructed.

EXAMPLES

The present invention will be more specifically explained with reference to the following examples. However, the following examples should be construed to be an aid for obtaining more specific understanding of the present invention, and the scope of the present invention is not no way limited by these examples.

Example 1

Preparation of in Vitro Virus (1)

<1> Preparation of 3'-terminal-end Portion of Nucleic Acid Portion (a) Synthesis of Phosphorylated Puromycin (pPur)

Materials:

Puromycin (3'-[α-amino-p-methoxyhydrocinnamamido]-3'-deoxy-N,N'-dimethyl-adenosine) was purchased from Sigma. Phosphorus oxychloride, and trimethyl phosphate were purchased from Wako Pure Chemicals.

Methods:

A solution formed by mixing phosphorus oxychloride (1.5 mmol) and trimethyl phosphate (11.4 mmol) was ice-cooled, and puromycin (0.3 mmol) was added thereto to mix sufficiently, and the mixture was allowed to react at 0° C. for 7 hours (Yoshikawa, M. et al. (1969) Bull. Chem. Soc. Jap. 42, 3505–3508). The reaction mixture was then added to an ice-cooled mixture of acetone (40 ml) and ether (20 ml) containing sodium perchlorate ($NaClO_4$, 0.4 g), and stirred sufficiently. Then, water (720 ml) was added to the mixture, and the mixture was stirred at 4° C. for 24 hours to hydrolyze the chlorine group. The product precipitated after the hydrolysis was separated by centrifugation, and washed with acetone and ether. The resulting white powder was dried in vacuo to afford phosphorylated puromycin with a yield of 70 to 90% based on the puromycin.

(b) Protection of Phosphorylated Puromycin by Acetylation

Materials:

Trifluoroacetic acid (TFA) was purchased from Nacalai Tesque. Trifluoroacetic anhydride (TFAA) was purchased from Wako Pure Chemicals.

Methods:

The dried phosphorylated puromycin (0.2 mmol) and TFA (5 ml) were mixed, and TFAA (2 ml) was added to the mixture at −10° C., followed by stirring. The mixture was allowed to react at room temperature for 1 hour with stirring (Weygand, F. & Gieger, R. (1956) Chem. Ber. 89, 647–652). The reaction was quenched by adding water (50 ml), and the TFA was removed by repeating a procedure comprising addition of water (10 ml) and evaporation to dryness under reduced pressure 5 times. Finally, water (50 ml) was added to the resulting product, followed by lyophilization to afford phosphorylated puromycin in which the amino group of the amino acid portion in puromycin and the 2'-hydroxyl group of the ribose portion were protected with acetyl groups with a yield of 50 to 60% based on the phosphorylated puromycin.

(c) Synthesis of dCpPur (2'-deoxycytidyl(3'→5') puromycin)

Materials:

BZ-DMT deoxycytidine ($N^4$-benzoyl-5'-O-(4,4'-dimethoxytrityl)-2'-deoxycytidine) was purchased from Sigma, and DCC (dicyclohexyl carbodiimide) was purchased from Watanabe Chemical. The pyridine was purchased from Nacalai Tesque.

Methods:

The phosphorylated puromycin protected with acetyl groups (40 μmol) and BZ-DMT deoxycytidine (600 μmol) were dehydrated by repeating a procedure comprising addition of pyridine (2 ml) and evaporation to dryness three times, and finally pyridine (2 ml) was added thereto. DCC (400 μmol) was added to the mixture with stirring, and the mixture was allowed to react at room temperature for 3 days to 2 weeks (Ralph, R. K. et al. (1965) J. Am. Chem. Soc. 87, 5661–5670; and Harris, R. J. et al. (1972) Can. J. Biochem. 50, 918–926). After the reaction, the DMT group was removed by a reaction with 80% acetic acid (5 ml) for two hours. Then, the acetyl group was removed by a reaction with concentrated aqueous ammonia/ethanol (6 ml, volume ratio: 2:1) at 20° C. for 2 days. The concentrated aqueous ammonia was removed by evaporation under reduced pressure, and the residue was dissolved in water (40 ml). The resulting solution was applied on a column packed with QAE-Sephadex A-25 (Pharmacia) and adsorbed thereon. Fractions containing the target product were eluted with 0.5 M triethylamine carbonate (TEAB, pH 7.5), lyophilized, and finally separated by HPLC to afford deprotected dCpPur with a yield of 1 to 5% based on the puromycin.

<2> Preparation of Nucleic Acid Portion (in vitro virus genome)

Two kinds of in vitro virus genomes, i.e., (1) one for bonding a nucleic acid portion and a protein portion in a site-directed manner, and (2) one for bonding a nucleic acid portion and a protein portion in a non-site-directed manner, were prepared.

Materials:

An *E. coli* cell-free protein synthesis system (*E. coli* S30 Extract System for Linear Templates) was purchased from Promega. T7 RNA polymerase, T4 DNA ligase, T4 DNA kinase, human placenta ribonuclease inhibitor, EcoRI, BamHI, and deoxyribonucleotides were purchased from Takara Shuzo. Restriction enzymes BstNI and BglII were purchased from New England Labs. As for [$^{35}$S]-methionine, and [$\gamma$-$^{32}$P]-ATP, those from Amersham, and as for Taq DNA polymerase, those from Kurabo and Grainer were used. As for the other biochemical reagents, those from Sigma and Wako Pure Chemicals were used. A plasmid containing the microtuble-binding region of human tau protein (4 repeats) (pAR3040) was prepared by picking up the full length gene of human tau protein from a cDNA library of human brain cloned in λ ZAPII by PCR, introducing the gene into a plasmid, amplifying only the 4 repeats region in the plasmid, and introducing the amplified product into a plasmid. As the PCR (polymerase chain reaction) apparatuses, Model PTC-100 (MJ Research) and Model ASTEC PC800 (Astec) were used.

(1) Preparation of Genome for Site-directed Bonding

A. Preparation of DNA for Mutated 4 Repeats Portion

1) A plasmid (pAR3040) comprising microtuble region (4 repeats) of human tau protein (Goedert, M. (1989) EMBO J. 8, 392–399) was constructed, and linearized by digestion with restriction enzymes BglII and BamHI.

2) The 4 repeats portion containing the T7 promoter region and the Shine-Dalgarno sequence was amplified by PCR from the genome prepared above. For this amplification, as primers, Left+ (SEQ ID NO: 1) was used for 5' side, and Right− (SEQ ID NO: 2) for the 3' side. Right− had such a sequence that the leucine before the ochre termination codon should be mutated into amber termination codon. The PCR conditions were 92° C./30 seconds for denaturation, 65° C./30 seconds for annealing, and 73° C./1 minute for elongation, and this cycle was repeated 30 times.

3) Then, the amplified genome was purified, and mutated by utilizing PCR in order to promote the incorporation of methionine and hence enhance detection of radioactive isotope. That is, primers Left− (SEQ ID NO: 3), and Right+ (SEQ ID NO: 4) containing a region desired to be mutated were synthesized. First, using the DNA of the above 2) as a template, it was amplified by PCR with primers Left+ and Left−, and the amplified DNA was designated as "Left". Amplification by PCR was also performed with primers Right+, and Right−, and the amplified DNA was designated as "Right". After 5% polyacrylamide denatured gel electrophoresis, "Left" and "Right" were excised form the gel, and extracted. The excised Left and Right were first amplified by PCR under the same conditions as mentioned above without primers. Further, 1 μl taken from this reaction mixture was used as a template, and it was amplified by PCR under the same conditions with primers Left+ and Right−. From the above procedure, DNA of the mutated 4 repeats portion in which the number of methionine was increased from one to four was prepared.

B. Ligation of Alanine Suppressor tRNA (Ala-sup tRNA), Containing Spacers Having Different Lengths to 4 Repeats Portion 1) The BaMH1 site located in the 3'-terminal-end sequence of the above 4 repeats portion obtained in the above A was digested with BamH1. Then, to remove 3'-terminal-end fragment at the BamH1 site, only the 4 repeats portion in 5'-terminal-end sequence was extracted and purified by using QIAquick PCR Purification Kit (QIAGEN).

2) The purified product of the above 1), and Spacer-A (SEQ ID NO: 5) which was phosphorylated at 5'-terminal end by T4 kinase were ligated by using T4 DNA ligase while they were backed with Spacer-B (SEQ ID NO: 6).

3) Spacer-C (SEQ ID NO: 7) which was phosphorylated by T4 kinase, and Spacer-B which had a region complementary to Spacer-C were ligated by using T4 DNA ligase. The reaction was performed at 15° C. for 2 hours. Then, the product was purified by ethanol precipitation.

4) The products of the above sections 2) and 3), Spacer-D (SEQ ID NO: 8), and sup tRNA (SEQ ID NO: 9) which was phosphorylated at 5'-terminal end were dissolved in T4 DNA ligase buffer, denatured at 85° C. for 2 minutes, and cooled on ice. After addition of T4 DNA ligase, it was allowed to react at 15° C. for 2 hours, and subjectedto phenol extraction, and ethanol precipitation.

5) The product obtained in the above 4) was used as a template, and amplification was carried out by PCR using the primer Left+, and a primer 3' Pur− (SEQ ID NO: 10) under the conditions of 92° C./30 seconds for denaturation, 65° C./30 seconds for annealing, and 73° C./1 minute for elongation, which cycle was repeated 30 times. The product was subjected to polyacrylamide denatured gel electrophoresis. Three regions A, B and C exhibiting different migration distances were excised, and DNA was extracted from the regions.

6) The DNAs extracted from A, B and C in the above 5) and having different lengths were used as templates and amplification were again carried out by PCR under the same conditions, and lengths of the products were determined by electrophoresis, and they were used as template DNA for transcription. As a result, it was found that the numbers of Spacer-C inserted into each product of the fractions were 0–5 for the fraction c, 6–14 for the fraction b, and 15–18 for the fraction a.

C. Preparation of RNA Genome and Ligation of dCpPur

The regions A, B and C obtained in the above B was transcribed into RNA at37° for 2 hours by using T7 polymerase. Further, the dCpPur obtained in the above <1> Preparation of 3'-terminal-end portion of the nucleic acid portion was phosphorylated in the presence of ATP by using T4 polynucleotide kinase at 15° C. for 24 hours, and ligated to the aforementioned transcribed RNA genome by using T4 RNA ligase at 4° C. for 50 hours. From this procedure, an RNA genome comprising sup tRNA having puromycin at its 3'-terminal end could be constructed.

(2) Preparation of Genome for Non-site-directed Bonding

A. Preparation of DNA and RNA for Mutated 4 Repeats Portion

DNA of the mutated 4 repeats portion was prepared principally the same method as the aforementioned (1) A. However, the termination codons were eliminated by changing the two termination codons, amber and ochre, to glutamine and lysine, respectively, and a new primer New/Right- (SEQ ID NO: 10) was synthesized in order to make the 3'-terminal-end sequence purine-rich, and used with Left+ for PCR amplification. The amplification by PCR was performed under the conditions of 92° C./30 seconds for denaturation, 65° C./30 seconds for annealing, and 73° C./1 minute for elongation, which cycle was repeated 30 times. This DNA was used as a template to obtain an RNA genome through a reaction at 37° C. for 2 hours utilizing T7 polymerase.

B. Ligation of Spacers 1 to 4

After a reaction at 36° C. for 1 hour with T4 polynucleotide kinase, of Spacer 1 which was a DNA composed of 21 nucleotides (SEQ ID NO: 11), Spacer 2 which was a DNA composed of 40 nucleotides (SEQ ID NO: 12), Spacer 3 which was a DNA composed of 60 nucleotides (SEQ ID NO: 13), or Spacer 4 which was a DNA composed of 80 nucleotides (SEQ ID NO: 14), the RNA obtained in the above A was ligated to the spacers through a reaction at 10° C. for 48 hours using T4 RNA ligase.

C. Ligation of Peptide Acceptor (P-Acceptor)

A peptide acceptor (P-Acceptor, SEQ ID NO: 15), which was a chimeric nucleic acid composed of 21-nucleotide DNA and 4-nucleotide RNA, i.e., 25 nucleotides in total, was synthesized in order to enhance the incorporation efficiency into ribosomes by ligating it at its 3'-terminal end to dCpPur. To phosphorylate the 5'-terminal end of P-Acceptor, it was reacted at 36° C. for 1 hour using T4 polynucleotide kinase. Then, the product was backed with Back3' (SEQ ID NO: 16) having a complementary sequence thereto, and ligated to the 3'-terminal end of each of the spacers prepared in the aforementioned B through a reaction at 16° C. for 2 hours using T4 RNA ligase. This P-Acceptor was also directly ligated to the 3'-terminal end of the RNA obtained in the above A through a reaction at 10° C. for 48 hours using T4 RNA ligase, and the product was designated as Non-Spacer genome.

D. Ligation of dCpPur

The dCpPur obtained in the above <1> Preparation of 3'-terminal-end portion of nucleic acid portion was phosphorylated by using T4 polynucleotide kinase at 15° C. for 24 hours, and ligated to the 3'-terminal end of each of the genomes prepared in the above C by using T4 RNA ligase at 4° C. for 50 hours. By this procedure, chimeric RNA genomes comprising puromycin at its 3'-terminal end could be constructed.

<3> Optimization of Nucleic Acid Portion

A. Site-directed Method

Each of the RNA genomes prepared in the above <2>, (1), which were classified into each of the lengths corresponding to the fractions a, b and c, was translated in 50 µl of *E. coli* cell-free translation system [*E. coli* S30 Extract Systems for Linear Templates (Promega)] containing biotinylated lysyl tRNA (Promega), and after addition of 5 mg of streptavidin coated magnetic beads (Dynabeads, Dynal) to each reaction tube, it was incubated at room temperature for 1 hour. Then, the Dynabeads were collected by a magnet, and the supernatant was aspirated. The remained Dynabeads were washed 2 times with B&W buffer (1000 µl). The beads were further washed twice with RT-PCR buffer (500 µl), and resuspended in RT-PCR buffer (500 µl). The suspension (50 µl) was transferred into a 500-µl Eppendorf tube, and after the Dynabeads were immobilized with a magnet, the supernatant was aspirated. To the remained Dynabeads, RT-PCR buffer, reverse transcriptase, and Taq polymerase [Access RT-PCR System (Promega)] were added. Reverse transcription was performed at 48° C. for 1 hours, and PCR was performed under the conditions of 94° C./30 seconds, 65° C./40 seconds, and 68° C./1 minute and 40 seconds, which cycle was repeated 40 times, using primers of Right+ (SEQ ID NO: 4) and 3' Pur– (SEQ ID NO: 10). The results of the analysis of the fractions a, b and c by electrophoresis were shown is FIG. 5.

Figure 5:
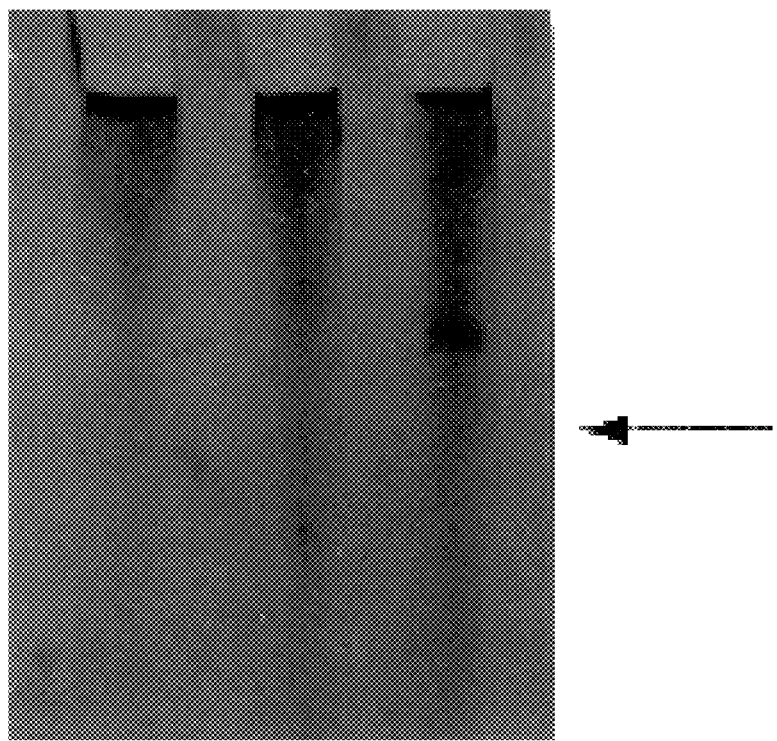
FIG. 5 is a photograph of electrophoresis image that shows spacer optimization in the site-directed method. It shows the results of 4% polyacrylamide gel electrophoresis (in the presence of 8 M urea) of a DNA obtained through a process comprising translation of each RNA genome having a spacer in a length corresponding to each of the prepared fractions a, b, and c in the presence of a biotinylated lysyl tRNA in an *E. coli* cell-free translation system, specific absorption on streptavidin-coated magnetic beads, reverse transcription, and amplification by PCR (staining was silver staining). Lane 1 is for the spacer length of fraction a (255–306 residues), Lane 2 is for the spacer length of fraction 2 (102–238 residues), and Lane 3 is for the spacer length of fraction c (0–85 residues).

A band was detected from the group of the fraction c (Lane 3 in FIG. 5). This band was separated from the gel by electrophoresis, ligated to "Left" having the T7 promoter and the Shine-Dalgarno region by PCR, and amplified by PCR using the primers Left+ (SEQ ID NO: 3) and 3' Pur– (SEQ ID NO: 10). This genome was designated as "Stranger".

Figure 6:
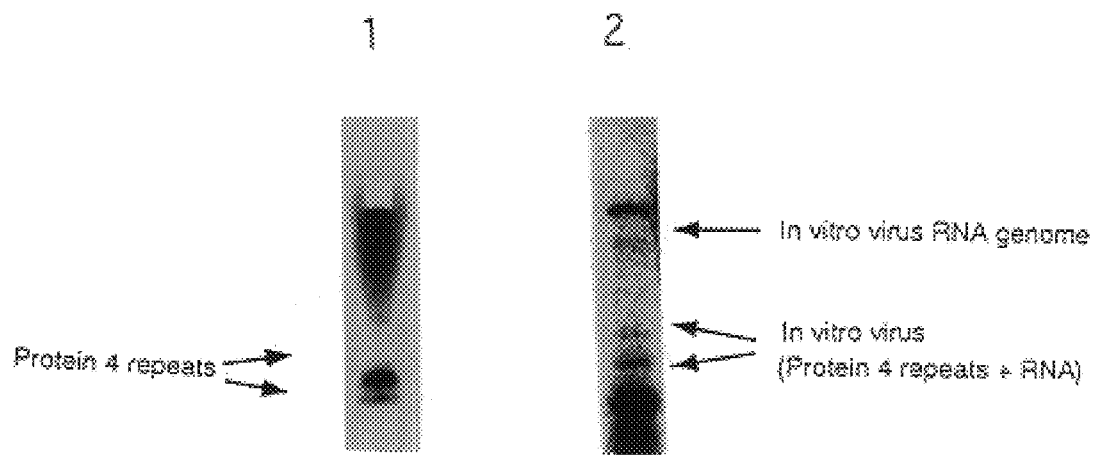
FIG. 6 is a photograph of electrophoresis image showing bonding of a nucleic acid portion and a protein portion in a site-directed method. The results were obtained by 18% polyacrylamide gel electrophoresis (in the presence of 8 M urea and SDS): Lane 1 for a translation product of mRNA encoding the 4 repeats region of a tau protein, which was obtained in an *E. coil* cell-free translation system while labeled with [$^{35}$S]-methionine, and Lane 2 for a translation pro duct of the mRNA whose 3'-terminal end was bonded to sup tRNA having puromycin, and whose 5'-terminal end was labeled with [$^{32}$P], which was obtained in an *E. coli* cell-free translation system.

Then, to examine whether the protein actually translated from Stranger was bonded to the mRNA portion (RNA genome portion), after transcription, it was ligated with pdCpPur at its 3'-terminal end using T4 RNA ligase, dephosphorylated at 5'-terminal end of RNA using HK phosphatase (Epicentre) at 30° C. for 1 hour, and labeled with [γ–$^{32}$P]-ATP using T4 polynucleotide kinase. The product was added to an *E. coli* cell-free translation system as mRNA, and allowed to react at 37° C. for 1 hour and 40 minutes. The results of 18% SDS-PAGE of the product are shown in FIG. 6. From the results, it can be seen that the nucleic acid portion (genotype) and the protein portion (phenotype) were bonded to form in vitro viruses, i.e., molecules that assign a genotype to a phenotype, at a rate of about 80% or more.

B. Non-site-directed Method

Figure 7:
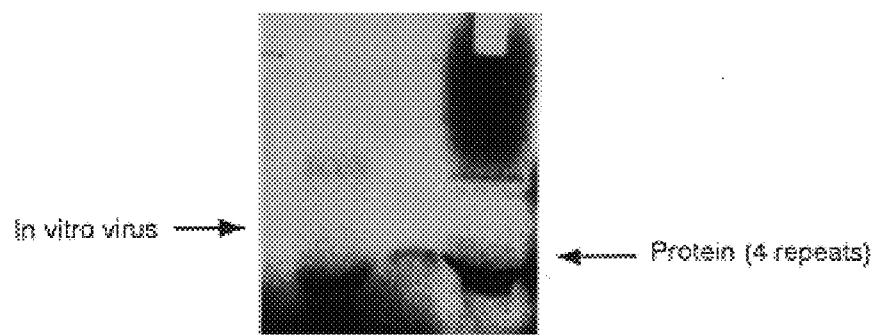
FIG. 7 is a photograph of electrophoresis image showing bonding of nucleic acid portion and protein portion in the non-site-directed method. The results were obtained by 18% polyacrylamide gel electrophoresis (in the presence of SDS): Lane 1 for a translation product of mRNA encoding the 4 repeats region of a tau protein, which was. obtained in an *E. coli* cell-free translation system, while labeled with [$^{35}$S]-methionine, and Lane 2 for a translation product of the mRNA whose 3'-terminal end was bonded through a spacer to puromycin labeled with [$^{32}$P] at the 5' end, which was obtained in an *E. coli* cell-free translation system, and Lane 3 for the translation product of Lane 2 digested with ribonuclease T2.

Because a short spacer was already used in the site-directed method, dCpPur, which had been phosphorylated at 5'-terminal end in the presence of [γ–$^{32}$P]-ATP using, T4 polynucleotide kinase, was ligated to the 3'-terminal end of "Non-spacer" RNA genome without a spacer through a reaction using T4 RNA ligase at 4° C. for 50 hours. The product was added to an *E. coli* cell-free translation system together with mRNA encoding the ordinary 4 repeats, and allowed to react at 37° C. for 1 hour and 30 minutes. This reaction mixture (10 µl) digested with ribonuclease T2, and an equal amount of the reaction mixture were electrophoresed by 18% SDS-PAGE, and analyzed by an image analyzer BAS2000 (Fujifilm) (FIG. 7).

As a result, as for the sample digested with ribonuclease T2, a band appeared at the same migration distance as that of the control, the 4 repeats labeled with [$^{35}$S]-methionine, because the sample contained the released protein portion. On the other hand, as for the sample not treated, a band appeared above the 4 repeats protein, i.e., it was found that the band reflected a clearly larger molecular weight. This band did not correspond to the labeled mRNA itself (about 400 nucleotides), because it migrated a longer distance than the tRNA. Therefore, it was identified as a substance composed of bonded RNA and protein. That is, these results demonstrated that the nucleic acid portion was bonded to the protein portion in a non-site-directed manner.

Example 2

Preparation of in Vitro Virus (2)

<1> Preparation of 3'-terminal-end Portion of Nucleic Acid Portion (a) Synthesis of rCpPur (ribocytidyl(3'→5')puromycin Materials:

Each material was purchased from the following manufacturers: Puromycin from Sigma, rC-β-amidite (N$^4$- benzoyl-5'-O-(4,4'-dimethoxytrityl)-2'-O-tert-butyldimethylsilyl)-cytidine-3'-O-[O-(2-cyanoethyl)-N,N'-diisopropyl-phosphoramidite]) from Japan PerSeptive, tetrazole from Japan Millipore, tetrabutylammonium fluoride from Aldrich, QAE-Sephadex from Pharmacia, and silica gel for chromatography from Merck.

Methods:

Puromycin (50 mg, 92 μmol) was dissolved in dry pyridine (2 ml), and dehydrated by evaporation under reduced pressure. This procedure was repeated three times. To this, 4% tetrazole solution in acetonitrile (15 ml) was added, and the mixture was stirred at room temperature. The reaction was monitored by silica gel thin layer, chromatography (TLC, developing solvent: chloroform:methanol=9:1). The reaction was usually finished in a day. After the reaction, the solvent was removed under reduced pressure. To the residue, 0.1 M solution of iodine in tetrahydrofuran/pyridine/water (80:40:2, 3 ml) was added, and the formed phosphite triester was oxidized with stirring at room temperature. One and a half hours later, the solvent was removed under reduced pressure, and the residue was extracted with chloroform. The extract was dried over anhydrous magnesium sulfate, and the solvent was removed under reduced pressure. The residue was subjected to silica gel column chromatography, and eluted with chloroform/methanol=90:10. The ribocytidylpuromycin (CpPur) having protection groups was eluted by silica gel TLC (developing solvent; chloroform:methanol=9:1) at an Rf of 0.32. Then, protection groups were removed. The ribocytidylpuromycin having protecting groups was first treated with 80% aqueous solution of acetic acid (0.5 ml) at room temperature for 1 hour. After the acetic acid was removed under reduced pressure, to the residue, a mixed solution of aqueous ammonia/ethanol=2:1 (0.5 ml) was added. After the mixture was left at room temperature for 15 hours, the solvent was removed under reduced pressure, and to the residue, 1 M solution of tetrabutylammonium fluoride in tetrahydrofuran (0.5 ml) was added to remove β-cyanoethyl group. Thirty minutes later, the solvent was removed under reduced pressure, and the residue was subjected to column chromatography using QAE-Sephadex, and eluted with 0 to 0.5 M linear gradient of triethylamine carbonate. The eluent was collected and lyophilized to afford 10 mg of ribocytidylpuromycin. The synthesized product was confirmed to be ribocytidylpuromycin by the facts that it afforded equimolar amounts of cytidine and puromycin-5'-phosphate after digestion with nuclease P1, and that molecular ions of [M+H]+ were appeared at m/z 777 in MALDI/TOF mass spectrometry.

<2> Nucleic acid Portion (preparation of in vitro virus genome)

Materials:

A cell-free protein synthesis system of rabbit reticulocyte lysate (Nuclease treated Rabbit reticulocyte lysate) was purchased from Promega. T7 RNA polymerase, T4 DNA ligase, T4 RNA ligase, T4 polynucleotide kinase, human placenta ribonuclease inhibitor, EcoRI, BamHI, and deoxyribonucleotides were purchased from Takara Shuzo. Restriction enzymes BstNI, and BglII were purchased from New England Labs. As for [$^{35}$S]-methionine, and [$^{32}$P]-γATP, those from Amersham, and as for Taq DNA polymerase, those from Kurabo and Grainer were used. As for the other biochemical reagents, those from Sigma and Wako Pure Chemicals were used. A plasmid containing the N-terminal half region of human tau protein (amino acid residue numbers 1–165) (pAR3040) was prepared by picking up the full length gene of human tau protein by PCR method from a cDNA library of human brain cloned in λZAPII, introducing the gene into a plasmid, amplifying only the N-terminal half region by PCR, and introducing the amplified product into a plasmid. As the PCR (polymerase chain reaction) apparatus, Model ASTEC PC800 (Astec) was used.

(1) Preparation of Genome

Figure 8:
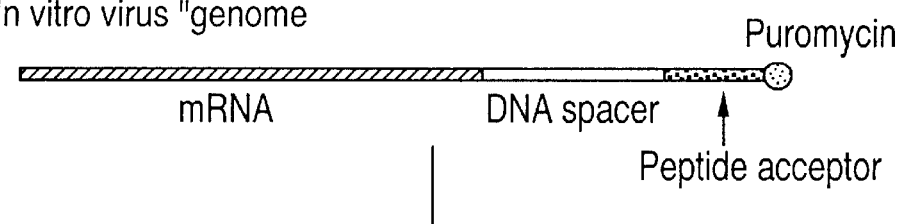
FIG. 8 shows an example of the method for constructing the molecule assigning the genotype to the phenotype (in vitro virus) according to the present invention.
Figure 8:
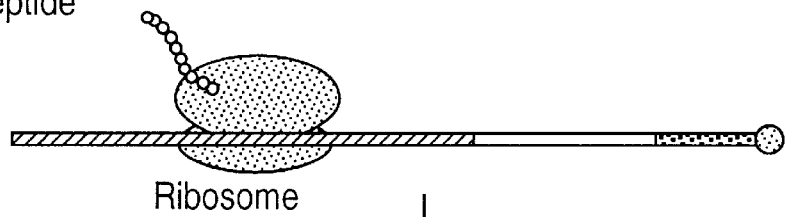
Figure 8:
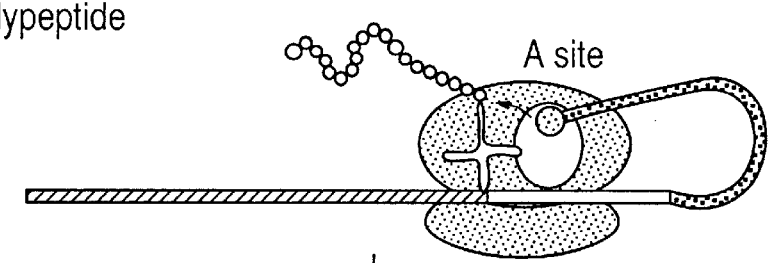
Figure 8:

A. Preparation of DNA for N-terminal Half Region mRNAs encoding the N-terminal half region of human tau protein (amino acid residues 1–165) with or without stop codon, which were ligated with spacer, peptide acceptor, and rCpPur at its 3'-terminal end, were constructed as follows (FIG. 8).

1) A plasmid into which the N-terminal half region of human tau protein (Goedert, M. (1989) EMBO J. 8, 392–399) (pAR3040) was introduced, was linearized by digestion with a restriction enzyme BglII.

2) The N-terminal half region (amino acid residue numbers 1–165) was amplified from the above genome by PCR. As primers, used were Left1 (SEQ ID NO: 18) for the 5' side, and Right1 (SEQ ID NO: 19) with stop codon, or Right2 (SEQ ID NO: 20) without stop codon for the 3' side. The PCR conditions consisted of 92° C./30 seconds for denaturation, 65° C./30 seconds for annealing, and 73° C./1 minute for elongation, and this cycle was repeated 30 times.

3) A DNA sequence composed of the promoter region of T7 RNA polymerase, Kozak sequence, and DNA sequence corresponding to amino acid residue numbers 1–25 of human tau protein connected in this order (SEQ ID NO: 21) was prepared by chemical synthesis.

4) The two kinds of purified DNA obtained in the procedures of the above 2) and 3) were connected by a two-step PCR as follows. That is, a mixture of the aforementioned two kinds of DNA was first amplified in the absence of primer, and subsequently amplified in the presence of primers of Left2 (SEQ ID NO: 22) and Right1 (SEQ ID NO: 19) or Right2 (SEQ ID NO: 20). From the above procedure, a DNA containing the promoter of T7 RNA polymerase and Kozak sequence at an upstream side of ORF of the N-terminal half region of human tau protein was prepared. An RNA was obtained through a reaction using this DNA as template, and T7 RNA polymerase at 37° C. for two hours.

B. Ligation of Spacer and Peptide Acceptor

Spacer 5 (SEQ ID NO: 23) and a peptide acceptor (P-Acceptor, SEQ ID NO: 15), which was a chimeric nucleic acid composed of 21-nucleotide DNA and 4-nucleotide RNA, i.e., 25 nucleotides in total, was chemically synthesized. The 5'-terminal end of the peptide acceptor was phosphorylated by reaction at 36° C. for 1 hour using T4 polynucleotide kinase, and the peptide acceptor was backed with a splint DNA (SEQ ID NO: 24) having a sequence complementary thereto, and ligated to the 3-terminal end of Spacer 5 through a reaction at 16° C. for 2 hours using T4 DNA ligase.

C. Ligation of RNA and Spacer-peptide Acceptor

The ligation product of Spacer 5-peptide acceptor obtained in the above B was phosphorylated at the 5-terminal end through a reaction at 36° C. for 1 hour using T4 polynucleotide kinase, and ligated to the RNA obtained in the above A through a reaction at 4° C. for 48 hours using T4 RNA ligase.

D. Ligation of rcpPur

The rCpPur obtained in the above <1> Preparation of 3'-terminal end portion of nucleic acid portion was phosphorylated through a reaction at 15° C. for 24 hours using T4 polynucleotide kinase, and ligated to the 3'-terminal end of the genome prepared in the above C through a reaction at 37° C. for 30 minutes using T4 RNA ligase. From this procedure, a chimera RNA genome having puromycin at its 3'-terminal end could be constructed.

E. Bonding of rCpPur to C-terminal End of N-terminal Half of human Tau Protein

Figure 9:
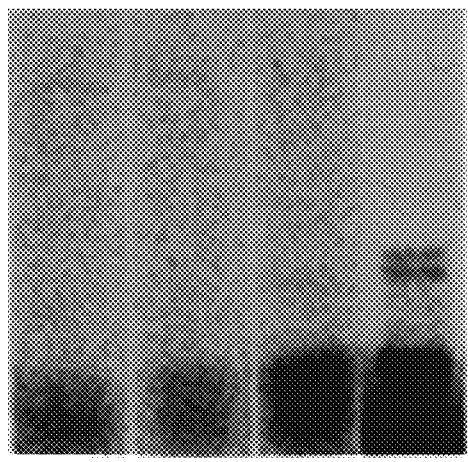
FIG. 9 is a photograph of electrophoresis image showing bonding of rcpPur to the C-terminal of the N-terminal half (1–165) of human tau protein. Three kinds of genomes, i.e., one having a stop codon but not a DNA spacer (the first lane from the left), one having neither of a stop codon and a DNA spacer (the second lane from the left), and one not having a stop codon but having a DNA spacer (the third lane from the left) each at the 3'-terminal end of mRNA encoding the N-terminal half (1–165) of human tau protein, were constructed, and translated in a cell-free translation system utilizing rabbit reticulocyte lysate in the presence of rCpPur labeled with $^{32}$P at 30° C. for 20 minutes. The translation products were analyzed by 11.25% SDS-PAGE. The lane at the right end shows the result for a product obtained by translation of the mRNA encoding the N-terminal half of human tau protein (1–165) in the presence of [$^{35}$S]-methionine under the same condition mentioned above.

It is considered that, in obtaining effective binding of a C-terminal end of a protein and an RNA encoding it, the distance between puromycin and a stop codon, and presence or absence of a stop codon would become important factors. Therefore, in order to examine effects of these factors, the following three kinds of genomes, mRNAs encoding the N-terminal half of human tau protein each (1) having a stop codon but not having a DNA spacer, (2) having neither of a stop codon and a DNA spacer, and (3) not having a stop codon but having a DNA spacer, at the 3'-terminal end were prepared. By using these three kinds of genomes, protein synthesis was performed in the presence of rCpPur labeled with $^{32}$P in a cell-free translation system utilizing rabbit reticulocyte lysate (FIG. 9). It was found that, when the 3'-terminal end did not have a DNA spacer, rCpPur was bound to the C-terminal of the protein with a similar efficiency regardless of the presence or absence of a stop codon. That is, in SDS-PAGE (SDS- polyacrylamide gel electrophoresis), the bands of the proteins bonded to rCpPur (the first and the second lanes from the left in FIG. 9) appeared at the same location as that of the protein monomer labeled with [$^{35}$S]-methionine (the most right lane in FIG. 9). On the other hand, if mRNA had a DNA spacer, rCpPur was bonded to the C-terminal end of the protein at an efficiency about three times higher than those obtained in the former two kinds of MRNA even without a stop codon (the third lane from the left, FIG. 9). This result can be considered to indicate that translation pausing of ribosome occurred on the DNA sequence, and as a result, rCpPur and the protein could be bonded efficiently. Further, this result suggests that, when a genome without a stop codon having a DNA spacer and rCpPur at its 3'-terminal end is used as mRNA in a cell-free translation system, puromycin at the 3'-terminal end of mRNA can efficiently be bonded to the C-terminal end of the corresponding translated protein.

<3> Construction of in Vitro Virus in cell-free Translation System

Figure 10:
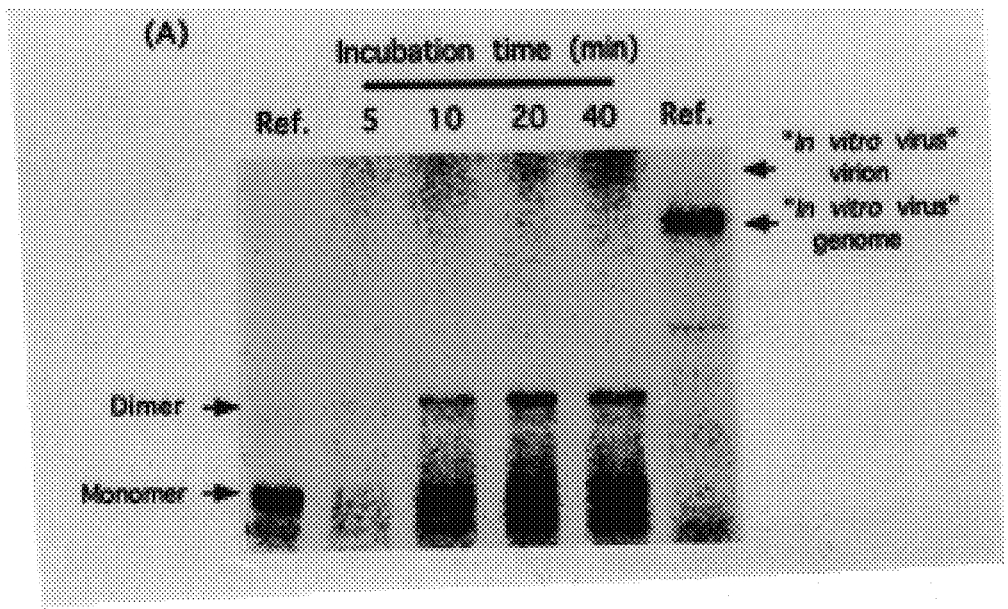
FIG. 10A and 10B, 10A is a photograph of electrophoresis image showing generation of in vitro viruses in a cell-free translation system. (A) shows a time course of generation of in vitro viruses. A genome composed of the mRNA encoding the N-terminal half of human tau protein (1–165), a DNA spacer (105 mer), a peptide acceptor, and rCpPur was translated in a cell-free translation system utilizing rabbit reticulocyte lysate and containing [$^{35}$S]-methionine, and the translation product was examined in a time course (at 5 minutes, 10 minutes, 20 minutes, and 40 minutes) at 30° C. The translation products were analyzed by 11.25% SDS-PAGE. The first lane from the left shows the result obtained by using the RNA encoding the N-terminal half of human tau protein (1–165) as mRNA, and examining incorporation of [$^{35}$S]-methionine into the protein under the same condition as mentioned above. The lane at the right end shows the result of in vitro virus genome labeled with $^{32}$P. (B) shows influence of concentration of in vitro virus genome for the generation of in vitro viruses. Lane 1 shows the results for a genome labeled with [$^{32}$P]-rCpPur at the 3'-terminal end, Lane 2 for a genome (1.2 μg) to which rCpPur was attached at its 3'-terminal end, Lane 3 for a genome (0.33 μg) to which rCpPur was attached at its 3'-terminal end, and Lane 4 for a genome (0.64 μg) to which rCpPur was attached at its 3'-terminal end. As for Lanes 2–4, the genomes were translated in a cell-free translation system utilizing rabbit reticulocyte lysate and containing [$^{35}$S]-methionine at 30° C. for 20 minutes. The translation products were analyzed by 11.25% SDS-PAGE.
Figure 10:
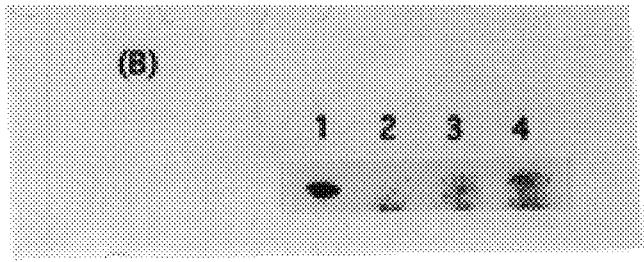

The genome constructed in the above <2> Nucleic acid portion (preparation of in vitro virus genome) composed of mRNA encoding the N-terminal half of human tau protein (1–165), DNA spacer (105 mer), peptide acceptor and rCpPur was translated by using rabbit reticulocyte lysate. When incorporation of [$^{35}$S]-methionine into the protein was examined first by using an RNA encoding the N-terminal half (1–165) of human tau protein as mRNA, bands appeared at locations corresponding to monomer (about 28 KDa) and dimer (about 55 KDa) of the N-terminal half (1–165). In this case, the monomer was the major product, and the dimer was observed in an extremely small amount (the first left lane in FIG. 10(A)). This result indicates that the RNA encoding the N-terminal half of human tau protein (1–165) functioned as mRNA. When the genome composed of mRNA encoding the N-terminal half (1–165) of human tau protein, DNA spacer (105 mer), peptide acceptor and rCpPur was translated in a similar cell-free translation system containing [$^{35}$S]-methionine, and the products were analyzed in time course (5 minutes, 10 minutes, 20 minutes, and 40 minutes), a new wide band appeared at a location slightly above that of the genome in addition to the bands at the location of the monomer and dimer (the first right lane in FIG. 10(A)). The intensity of this band increased with increase of reaction time (the second to fifth lanes from the left in FIG. 10(A)), and increase of the genome amount (Lanes 3 and 4 in FIG. 10(B)). These results indicate that the genome was bonded to the C-terminal end of the protein with a covalent bond through puromycin. This also means that a genotype was covalently bound to a phenotype. That is, a molecule that assigns a genotype to a phenotypes was formed. The present inventors designated this assigning molecule as in vitro virus. When the effect of the length of DNA spacer on the formation of in vitro virus was examined, it was found that the in vitro virus was not formed efficiently with a length of about 80 mer, and it required a length of at least 100 mer.

Figure 11:
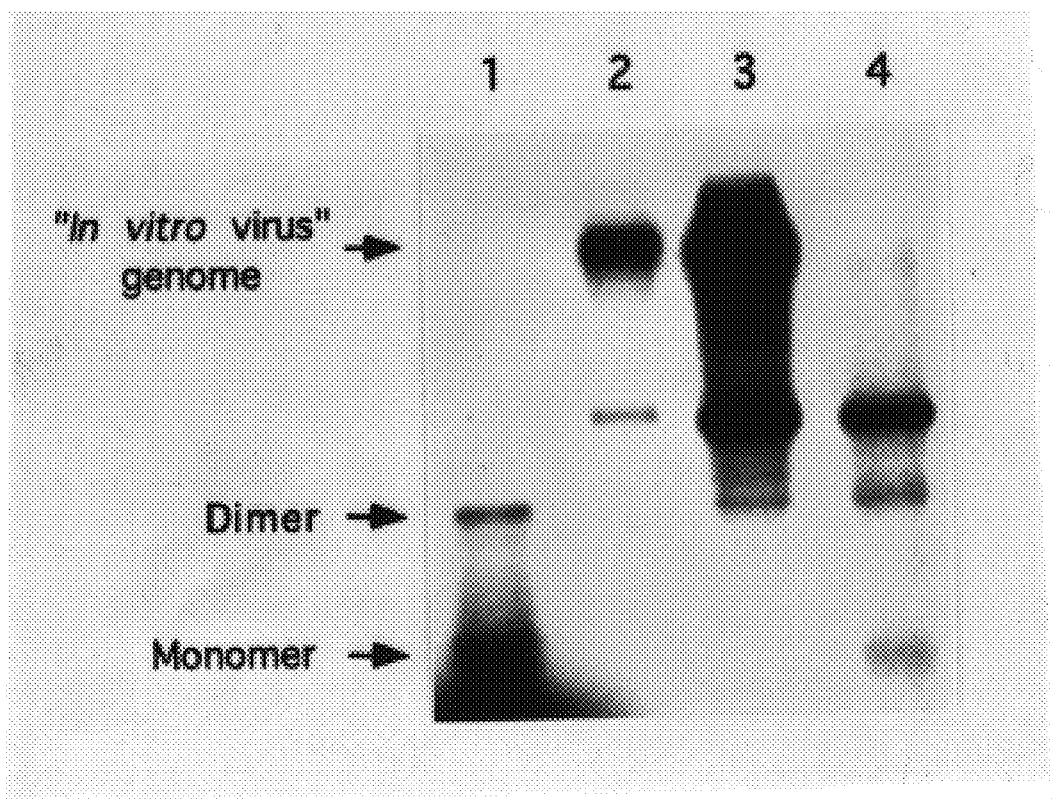
FIG. 11 is a photograph of electrophoresis image showing generation of in vitro viruses in a cell-free translation system. An in vitro virus genome composed of the mRNA encoding the N-terminal half (1–165) of human tau protein, a DNA spacer (105 mer), a peptide acceptor, and [$^{32}$P]-rCpPur was translated by utilizing rabbit reticulocyte lysate at 30° C. for 20 minutes. The translation products were analyzed by 11.25% SDS-PAGE. The bonding of the genome and the protein could be confirmed by digestion with mung bean nuclease. When the translation product (Lane 3) was digested with mung bean nuclease, bands appeared (Lane 4) at the locations corresponding to monomer and dimer (Lane 1) of the N-terminal half of human tau protein (1–165). Lane 2 shows the result for an in vitro virus genome labeled with $^{32}$P.

Further, the generation of in vitro virus was confirmed by using rCpPur labeled with $^{32}$P That is, a genome composed of mRNA encoding the N-terminal half (1–165) of human tau protein, DNA spacer (105 mer), peptide acceptor, and [$^{32}$P]-rCpPur was translated by using rabbit reticulocyte lysate. The bonding of the genome and the protein was confirmed by digestion with mung bean nuclease. That is, when the translation product (Lane 3 in FIG. 11) was digested with mung bean nuclease, bands appeared at the locations corresponding to monomer and dimer (Lane 1 in FIG. 11) of the N-terminal half (1–165) of human tau protein (Lane 4 in FIG. 11). This indicates that the rCpPur labeled with $^{32}$P was attached to the 3'-terminal end of the protein. Also from this result, it was confirmed that the genome was bound to the C-terminal end of the protein with a covalent bond through puromycin. The efficiency of the binding was estimated to be about 10%. Because in vitro virus genome having a concentration of 40 to 100 pmol/ml can be prepared, generated in vitro viruses would consist of a population containing 2.4 to $6\times10^{12}$ of mutants, and this number corresponds to 10000 times of that obtained in the phage display method (Scott, J. K. & Smith, G. P. (1990) Science 249, 386–390). The genotype assignment to phenotype has advantages, for example, it eliminates the problem concerning the permeability, and it enables incorporation of various non-naturally-occurring amino acids, and therefore it enables synthesis of an extremely large number of mutants, or creation of various functional proteins.

Example 3

Protein Evolution Simulation Method Utilizing in Vitro Viruses

The protein evolution simulation method utilizing in vitro viruses comprises, as shown in FIG. 12, (1) construction of in vitro virus genomes, (2) completion of in vitro viruses, (3) selection process, (4) introduction of mutation, and (5) amplification, and it allows modification and creation of functional proteins. In particular, repetition of these steps allows efficient modification and creation of functional proteins. Among these steps, the steps of (1) and (2) were specifically explained in Examples 1 and 2 mentioned above. Therefore, the steps (3), (4) and (5) will be explained in this example.

First, it was examined whether peptides specific to an antibody were selected. Specifically, mouse IgG was used as the antibody, and the known ZZ region of protein A (Nilsson, B., et al., (1987) Protein Eng., 1, 107–113) was used as a peptide sequence to be specifically bound to the antibody. As a control, N-terminal region (1–105) of human tau protein (Goedert, M. (1989) EMBO J. 8, 392–399) was used. According to the construction methods of in vitro viruses described in the above Examples 1 and 2, in vitro virus genomes encoding the ZZ region of protein A and the N-terminal region (1–105) of human tau protein were prepared. With different ratios of the in vitro virus genome encoding the ZZ region of protein A and the in vitro virus genome encoding the N-terminal region (1–105) of human tau protein varying as 1:1, 1:10, 1:100, 1:1000 or the like, they were translated in a cell-free translation system utilizing rabbit reticulocyte lysate at 30° C. for 10 minutes. Then, the translation product was diluted, and centrifuged to remove insoluble fractions, and the supernatant was added to a microplate coated with mouse IgG (blocked with bovine serum albumin beforehand), and left stand at 4° C. for 2 hours. Then, the translation product was removed from the microplate, and it was washed with a washing buffer (50 mM Tris/acetic acid, pH 7.5, 150 mM NaCl, 10 mM EDTA, 0.1% Tween 20) for 6 times in total, and eluted 2 times with an elution buffer (1 M acetic acid, pH 2.8). The eluted solution was subjected to ethanol precipitation, and the precipitates were dissolved in sterile water (20 µl), and used as a template for reverse transcription PCR. The reverse transcription PCR was performed by using reverse transcriptase (Avian Mieloblastosis Virus Reverse Transcriptase, Promega), DNA polymerase (Tfl DNA Polymerase, Promega), and RT+ (SEQ ID NO: 25) and RT– (SEQ ID NO: 26) as primers. Following a reaction at 48° C. for 40 minutes, the reverse transcriptase was inactivated with a treatment at 94° C. for 5 minutes, and a cycle of 94° C. for 30 seconds, 66° C. for 40 seconds, and 72° C. for 40 seconds was repeated 30 times. The obtained PCR product was electrophoresed at 55° C. on 4% polyacrylamide gel containing 8 M urea, and observed by silver staining. As a result, it was found that the in vitro virus genome containing the ZZ region of protein A could be amplified even in an amount of one-100th of the control genome, i.e., the in vitro virus genome containing the N-terminal region (1–105) of human tau protein. This result indicates that the in vitro virus genome containing the ZZ region of protein A was specifically bound to mouse IgG through the translated ZZ region of protein A. Therefore, it was confirmed that the in vitro viruses could be selected. Introduction of mutation and amplification can be performed by using the already-established error-prone PCR (Leung, D. W., et al., (1989) J. Methods Cell Mol. Biol., 1, 11–15), Sexual PCR (Stemmer, W. P. C. (1994) Proc. Natl. Acad. Sci. If USA 91, 10747–10751) or the like. Therefore, it was verified that the protein evolution simulation method shown in FIG. 12 was feasible.

According to the present invention, a molecule assigning a genotype (nucleic acid portion) to a phenotype (protein portion), and construction methods therefor are provided. There are also provided a protein evolution simulation method utilizing molecules that assign a genotype to a phenotype (in vitro viruses) constructed according to the present invention, which comprises selecting the in vitro viruses by the in vitro selection method, amplifying the gene portion of an extremely small amount of the selected in vitro viruses by reverse transcription PCR, and further performing amplification while introducing a mutation, and the like. The molecule assigning the genotype to the phenotype, the protein evolution simulation method utilizing it and the like of the present invention are an extremely useful substance or experimental system for evolutionary molecular engineering, i.e., modification of functional biopolymers such as enzymes, antibodies, and ribozymes, and creation of biopolymers having functions which cannot be found in living organisms.

What is claimed is:

1. A molecule comprising a nucleic acid portion and a protein portion covalently bound to said nucleic acid portion through a substance having a chemical structure of a member selected from the group consisting of puromycin, 3'-N-aminoacylpuromycin aminonucleoside, and 3'-N-aminoacyladenosine aminonucleoside, wherein said nucleic acid portion comprises a polymer of nucleoside, and said protein portion is encoded by said nucleic acid portion.

2. The assigning molecule according to claim 1, wherein a 3'-terminal end of the nucleic acid portion and a C-terminal end of the protein portion are bonded with a covalent bond.

3. The molecule according to claim 1 or 2, wherein a 3'-terminal end of the nucleic acid portion covalently bonded to a C-terminal end of the protein portion is puromycin.

4. The molecule according to claim 1, wherein the nucleic acid portion comprises a gene composed of RNA, and a suppressor tRNA bonded to the gene through a spacer.

5. The molecule according to claim 1, wherein the nucleic acid portion comprises a gene composed of RNA, and a spacer composed of DNA and RNA.

6. The molecule according to claim 1, wherein the nucleic acid portion comprises a gene composed of RNA, and a spacer composed of DNA and polyethylene glycol.

7. The molecule according to claim 1, wherein the nucleic acid portion comprises a gene composed of RNA, and a spacer composed of a double-stranded DNA.

8. The molecule according to claim 1, wherein the nucleic acid portion comprises a gene composed of RNA, and a spacer composed of a double strand of RNA and a short chain peptide nucleic acid (PNA) or DNA.

9. The molecule according to claim 1, wherein the nucleic acid portion comprises a gene composed of DNA, and a spacer composed of DNA and RNA.

10. The molecule according to claim 1 or 2, wherein a 3'-terminal end of the nucleic acid portion covalently bonded to a C-terminal end of the protein portion is a substance having the ability to bind to the C-terminal of a synthesized protein when protein synthesis is carried out in a cell-free protein synthesis system.

11. The molecule according to claim 1 or 2, wherein a 3' terminal end of the nucleic acid portion covalently bonded to a C-terminal end of the protein portion is 3'-N-aminoacylpuromycin aminonucleoside or 3'-N-aminoacyladenosine aminonucleoside.

12. The molecule according to claim 2, wherein the covalent bond is formed by a cell-free protein synthesis system.

13. The molecule according to claim 4, wherein the suppressor tRNA comprises an anticodon corresponding to a termination codon of the gene.

14. A method for constructing the molecule as defined in claim 4, which comprises (a) bonding a DNA comprising a sequence corresponding to a suppressor tRNA, to a 3'-terminal end of a DNA containing a gene through a spacer, (b) transcribing the obtained DNA bonded product into RNA, (c) bonding, to a 3'-terminal end of the obtained RNA, a nucleoside or a substance having a chemical structure analogous to that of a nucleoside, which can be covalently bound to an amino acid or a substance having a chemical structure analogous to that of an amino acid, and (d) performing protein synthesis in a cell-free protein synthesis system using the obtained bonded product as MRNA to bond a nucleic acid portion containing the gene to a translation product of the gene, thereby constructing the molecule.

15. A method for constructing the molecule as defined in claim 5, which comprises (a) preparing a DNA containing a gene which has no termination codon, (b) transcribing the prepared DNA into RNA, (c) bonding a chimeric spacer composed of DNA and RNA to a 3'-terminal end of the obtained RNA, (d) bonding, to a 3'-terminal end of the obtained bonded product, a nucleoside or a substance having a chemical structure analogous to that of a nucleoside, which can be covalently bound to an amino acid or a substrate having a chemical structure analogous to that of an amino acid, and (e) performing protein synthesis in a cell-free protein synthesis system using the obtained bonded product as mRNA to bond a nucleic acid portion containing the gene to a translation product of the gene, thereby constructing the molecule.

16. A method for constructing the molecule as defined in claim 6, which comprises (a) preparing a DNA containing a gene which has no termination codon, (b) transcribing the prepared DNA into RNA, (c) bonding a chimeric spacer composed of DNA and polyethylene glycol to a 3'-terminal end of the obtained RNA, (d) bonding, to a 3'-terminal end of the obtained bonded product, a nucleoside or a substance having a chemical structure analogous to that of a nucleoside, which can be covalently bound to an amino acid or a substance having a chemical structure analogous to that of an amino acid, and (e) performing protein synthesis in a cell-free protein synthesis system using the obtained bonded product as mRNA to bond a nucleic acid portion containing the gene to a translation product of the gene, thereby constructing the molecule.

17. A method for constructing the molecule as defined in claim 7, which comprises (a) preparing a DNA containing a gene which has no termination codon, (b) transcribing the prepared DNA into RNA, (c) bonding a spacer composed of double-stranded DNA to a 3'-terminal end of the obtained RNA, (d) bonding, to a 3'-terminal end of the obtained bonded product, a nucleoside or a substance having a chemical structure analogous to that of a nucleoside, which can be covalently bound to an amino acid or a substance having a chemical structure analogous to that of an amino acid, and (e) performing protein synthesis in a cell-free protein synthesis system using the obtained bonded product as mRNA to bond a nucleic acid portion containing the gene to a translation product of the gene, thereby constructing the molecule.

18. A method for constructing the molecule as defined in claim 8, which comprises (a) preparing a DNA containing a gene which has no termination codon, and a nucleotide sequence of a spacer, (b) transcribing the prepared DNA into RNA, (c) bonding, to a 3'-terminal end of the obtained RNA, a nucleoside or a substance having a chemical structure analogous to that of a nucleoside, which can be covalently bound to an amino acid or a substance having a chemical structure analogous to that of an amino acid, (d) adding a short chain PNA or DNA to a 3'-terminal end side portion of the gene in the obtained RNA bonded product to form a double-stranded chain, and (e) performing protein synthesis in a cell-free protein synthesis system using the obtained bonded product as MRNA to bond a nucleic acid portion containing the gene to a translation product of the gene, thereby constructing the molecule.

19. The construction method according to claim 14 or 15, wherein the nucleoside or the substance having the chemical structure analogous to that of the nucleoside is puromycin.

20. A method for protein evolution simulation, which comprises a construction step for constructing molecules from a DNA containing a gene by the construction method as defined in any one of claims 14, 15, 16, 17 and 18, a selection step for selecting the molecules obtained in the construction step, a mutation introduction step for introducing a mutation into a gene portion of a molecule selected in the selection step, and an amplification step for amplifying the gene portion obtained in the mutation introduction step, thereby simulating protein evolution.

21. A method for assaying protein/protein or protein/nucleic acid intermolecular action, which comprises a construction step for constructing molecules by the construction method of any one as defined in claims 14, 15, 16, 17 and 18, and an assay step for examining intermolecular action of the molecules obtained in the construction step with another protein or nucleic acid, thereby assaying protein/protein or protein/nucleic acid intermolecular action.

22. The method for protein evolution simulation according to claim 20, wherein the construction step, the selection step, the mutation introduction step and the amplification step are repeatedly performed by providing the DNA obtained in the amplification step to the construction step.

23. The method for protein evolution simulation according to claim 20, wherein the selection step is conducted using a target substance which is bound to a solid-state surface.

24. An apparatus for performing a method for protein evolution simulation, which comprises a means for constructing molecules, said means comprising a first bonding means for bonding a DNA comprising a sequence corresponding to a suppressor tRNA to a 3'-terminal end of a DNA containing a gene through a spacer, a transcription means for transcribing the DNA bonded product obtained by the first bonding means into RNA, a second bonding means for bonding, to a 3'-terminal end of the RNA obtained by the transcription means, a nucleoside or a substance having a chemical structure analogous to that of a nucleoside, which can be covalently bound to an amino acid or a substance having a chemical structure analogous to that of an amino acid, and a third bonding means for performing protein synthesis in a cell-free protein synthesis system using the bonded product obtained by the second bonding means as MRNA to bond a nucleic acid portion containing the gene to a translation product of the gene, or a means for constructing assigning molecules, said means comprising a transcription means for transcribing a DNA containing a gene into RNA, a first bonding means for bonding a chimeric spacer composed of DNA and RNA, a chimeric spacer composed of DNA and polyethylene glycol, a double-stranded spacer composed of DNA, or a double-stranded spacer composed of RNA and PNA or DNA to a 3'-terminal end of the RNA obtained by the transcription means, a second bonding means for bonding, to a 3'-terminal end of the RNA-spacer bonded product obtained by the first bonding means, a nucleoside or a substance having a chemical structure analogous to that of a nucleoside, which can be covalently bound to an amino acid or a substance having a chemical structure analogous to that of an amino acid, and a third bonding means for performing protein synthesis in a cell-free protein synthesis system using the bonded product obtained by the second bonding means as MRNA to bond a nucleic acid portion containing the gene to a translation product of the gene; a selection means for selecting the constructed molecules; a mutation introduction means for introducing a mutation into a gene portion of a molecule selected; and an amplification means for amplifying the gene portion to which the mutation is introduced.

* * * * *

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
      (A) LENGTH: 33
      (B) TYPE: nucleic acid
      (C) STRANDEDNESS: single
      (D) TOPOLOGY: linear (ii) MOLECULE TYPE: other nucleic acid
      (A) DESCRIPTION: synthetic DNA (ix) FEATURE:
      (D) OTHER INFORMATION: T7 promoter upstream (xi) SEQUENCE DESCRIPTION: SEQ ID NO: 1:

GAGCATAGAT CTCGATCCCG CGAAATTAAT ACG      33

(2) INFORMATION FOR SEQ ID NO: 2:

(i) SEQUENCE CHARACTERISTICS:
      (A) LENGTH: 33
      (B) TYPE: nucleic acid
      (C) STRANDEDNESS: single
      (D) TOPOLOGY: linear (ii) MOLECULE TYPE: other nucleic acid
      (A) DESCRIPTION: synthetic DNA (ix) FEATURE:
            (D) OTHER INFORMATION: includes a termination codon (xi) SEQUENCE DESCRIPTION: SEQ ID NO: 2:

GCAGCCGGAT CCTTACTACT TGTGGGTTTC AAT                              33

(2) INFORMATION FOR SEQ ID NO: 3:

(i) SEQUENCE CHARACTERISTICS:
        (A) LENGTH: 33
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA (ix) FEATURE:
        (D) OTHER INFORMATION: includes an initiation codon;
            complementary to SEQ ID NO: 4

(xi) SEQUENCE DESCRIPTION: SEQ ID NO: 3:

GGACATGACA TTCATCATGT CTGGCATATG TAT                              33

(2) INFORMATION FOR SEQ ID NO: 4:

(i) SEQUENCE CHARACTERISTICS:
        (A) LENGTH: 33
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA (ix) FEATURE:
        (D) OTHER INFORMATION: includes an initiation codon;
            complementary to SEQ ID NO: 3

(xi) SEQUENCE DESCRIPTION: SEQ ID NO: 4:

ATACATATGC CAGACATGAT GAATGTCATG TCC                              33

(2) INFORMATION FOR SEQ ID NO: 5:

(i) SEQUENCE CHARACTERISTICS:
        (A) LENGTH: 16
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA (ix) FEATURE:
        (D) OTHER INFORMATION: has a portion complementary to
            SEQ ID NO: 6

(xi) SEQUENCE DESCRIPTION: SEQ ID NO: 5:

GATCTATTTC TTATTC                                                 16

(2) INFORMATION FOR SEQ ID NO: 6:

(i) SEQUENCE CHARACTERISTICS:
        (A) LENGTH: 17
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA

```
        (ix) FEATURE:
             (D) OTHER INFORMATION: has an initiation codon;
                 complementary to SEQ ID NO: 5

(xi) SEQUENCE DESCRIPTION: SEQ ID NO: 6:

GAAGAGAATA AGAAATA                                                       17

(2) INFORMATION FOR SEQ ID NO: 7:

(i) SEQUENCE CHARACTERISTICS:
            (A) LENGTH: 17
            (B) TYPE: nucleic acid
            (C) STRANDEDNESS: single
            (D) TOPOLOGY: linear (ii) MOLECULE TYPE: other nucleic acid
            (A) DESCRIPTION: synthetic DNA (ix) FEATURE:
            (D) OTHER INFORMATION: has a portion complementary to
                SEQ ID NO: 6

(xi) SEQUENCE DESCRIPTION: SEQ ID NO: 7:

TCTTCTATTT CTTATTC                                                       17

(2) INFORMATION FOR SEQ ID NO: 8:

(i) SEQUENCE CHARACTERISTICS:
            (A) LENGTH: 30
            (B) TYPE: nucleic acid
            (C) STRANDEDNESS: single
            (D) TOPOLOGY: linear (ii) MOLECULE TYPE: other nucleic acid
            (A) DESCRIPTION: synthetic DNA (ix) FEATURE:
            (D) OTHER INFORMATION: has a portion complementary to
                SEQ ID NO: 9

(xi) SEQUENCE DESCRIPTION: SEQ ID NO: 8:

GGGTAAACGA ATGAACAAGA ATAAGAAATA                                          30

(2) INFORMATION FOR SEQ ID NO: 9:

(i) SEQUENCE CHARACTERISTICS:
            (A) LENGTH: 108
            (B) TYPE: nucleic acid
            (C) STRANDEDNESS: single
            (D) TOPOLOGY: linear (ii) MOLECULE TYPE: other nucleic acid
            (A) DESCRIPTION: synthetic DNA (ix) FEATURE:
            (D) OTHER INFORMATION: has a sequence of an alanyl tRNA (xi) SEQUENCE DESCRIPTION: SEQ ID NO: 9:

TTGTTCATTC GTTTACCCGG GGCTATAGCT CAGCTGGGAG AGCGCCTGCT TCTAACGCAG         60

GAGGTCTGCG GTTCGATCCC GCGTAGCTCC ACCAGGAGGC GACTAGCT                    108

(2) INFORMATION FOR SEQ ID NO: 10:

(i) SEQUENCE CHARACTERISTICS:
            (A) LENGTH: 23
            (B) TYPE: nucleic acid
            (C) STRANDEDNESS: single
            (D) TOPOLOGY: linear (ii) MOLECULE TYPE: other nucleic acid
```

(A) DESCRIPTION: synthetic DNA (ix) FEATURE:
          (D) OTHER INFORMATION: has a 3'-side sequence of an
              alanyl tRNA (xi) SEQUENCE DESCRIPTION: SEQ ID NO: 10:

GTGGAGCTAC GCGGGATCGA ACC                                          23

(2) INFORMATION FOR SEQ ID NO: 11:

(i) SEQUENCE CHARACTERISTICS:
          (A) LENGTH: 25
          (B) TYPE: nucleic acid
          (C) STRANDEDNESS: single
          (D) TOPOLOGY: linear (ii) MOLECULE TYPE: other nucleic acid
          (A) DESCRIPTION: synthetic DNA (ix) FEATURE:
          (D) OTHER INFORMATION: has no initiation codon (xi) SEQUENCE DESCRIPTION: SEQ ID NO: 11:

GCAGCCGGAT CCTTTCTGCT TGTGG                                        25

(2) INFORMATION FOR SEQ ID NO: 12:

(i) SEQUENCE CHARACTERISTICS:
          (A) LENGTH: 21
          (B) TYPE: nucleic acid
          (C) STRANDEDNESS: single
          (D) TOPOLOGY: linear (ii) MOLECULE TYPE: other nucleic acid
          (A) DESCRIPTION: synthetic DNA (ix) FEATURE:
          (D) OTHER INFORMATION: has a sequence partly
              complementary to SEQ ID NO: 17

(xi) SEQUENCE DESCRIPTION: SEQ ID NO: 12:

CTTTAATGAC CTCCCCTCTC C                                            21

(2) INFORMATION FOR SEQ ID NO: 13:

(i) SEQUENCE CHARACTERISTICS:
          (A) LENGTH: 40
          (B) TYPE: nucleic acid
          (C) STRANDEDNESS: single
          (D) TOPOLOGY: linear (ii) MOLECULE TYPE: other nucleic acid
          (A) DESCRIPTION: synthetic DNA (ix) FEATURE:
          (D) OTHER INFORMATION: has a sequence partly
              complementary to SEQ ID NO: 17

(xi) SEQUENCE DESCRIPTION: SEQ ID NO: 13:

CTTTAATAAT TTTTTTTTTT TTTAATGACC TCCCCTCTCC                        40

(2) INFORMATION FOR SEQ ID NO: 14:

(i) SEQUENCE CHARACTERISTICS:
          (A) LENGTH: 60
          (B) TYPE: nucleic acid
          (C) STRANDEDNESS: single
          (D) TOPOLOGY: linear (ii) MOLECULE TYPE: other nucleic acid (A) DESCRIPTION: synthetic DNA (ix) FEATURE:
        (D) OTHER INFORMATION: has a sequence partly
            complementary to SEQ ID NO: 17

(xi) SEQUENCE DESCRIPTION: SEQ ID NO: 14:

CTTTAATAAT TTTTTTTTTT TTTTTTTTTT TTTTTTTTTT TTTAATGACC TCCCCTCTCC        60

(2) INFORMATION FOR SEQ ID NO: 15:

(i) SEQUENCE CHARACTERISTICS:
        (A) LENGTH: 80
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA (ix) FEATURE:
        (D) OTHER INFORMATION: has a sequence partly
            complementary to SEQ ID NO: 17

(xi) SEQUENCE DESCRIPTION: SEQ ID NO: 15:

CTTTAATAAT TTTTTTTTTT TTTTTTTTTT TTTTTTTTTT TTTTTTTTTT TTTTTTTTTT        60

TTTAATGACC TCCCCTCTCC                                                    80

(2) INFORMATION FOR SEQ ID NO: 16:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA (ix) FEATURE:
        (B) LOCATION: 22..25
        (D) OTHER INFORMATION: RNA (xi) SEQUENCE DESCRIPTION: SEQ ID NO: 16:

CTTACTGTCT TTTTTTTTTT TGAGC                                              25

(2) INFORMATION FOR SEQ ID NO: 17:

(i) SEQUENCE CHARACTERISTICS:
        (A) LENGTH: 33
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA (ix) FEATURE:
        (D) OTHER INFORMATION: has a sequence partly
            complementary to SEQ ID NO: 16

(xi) SEQUENCE DESCRIPTION: SEQ ID NO: 17:

AAAAAAGACA GTAAGGGAGA GGGGAGGTCA TTA                                     33

(2) INFORMATION FOR SEQ ID NO: 18:

(i) SEQUENCE CHARACTERISTICS:
        (A) LENGTH: 24
        (B) TYPE: nucleic acid
        (C) STRANDEDNESS: single

```
        (D) TOPOLOGY: linear (ii) MOLECULE TYPE: other nucleic acid
        (A) DESCRIPTION: synthetic DNA (ix) FEATURE:
        (D) OTHER INFORMATION: includes an N-terminal
            initiation codon in an N-terminal-half region of a
            tau protein (xi) SEQUENCE DESCRIPTION: SEQ ID NO: 18:

ATGGCTGAGC CCCGCATGGA GTTC                                              24

(2) INFORMATION FOR SEQ ID NO: 19:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA (ix) FEATURE:
        (D) OTHER INFORMATION: includes a C-terminal
            termination codon in an N-terminal-half region of a
            tau protein (xi) SEQUENCE DESCRIPTION: SEQ ID NO: 19:

CTCTGCCACT TACTAGGGCT CCCG                                              24

(2) INFORMATION FOR SEQ ID NO: 20:

(i) SEQUENCE CHARACTERISTICS:
        (A) LENGTH: 23
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA (ix) FEATURE:
        (D) OTHER INFORMATION: includes a C-terminal
            termination codon in an N-terminal-half region of a
            tau protein (xi) SEQUENCE DESCRIPTION: SEQ ID NO: 20:

CTCTGCCACC TTCTTGGGCT CCC                                               23

(2) INFORMATION FOR SEQ ID NO: 21:

(i) SEQUENCE CHARACTERISTICS:
        (A) LENGTH: 118
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA (ix) FEATURE:
        (D) OTHER INFORMATION: includes a promoter region of T7
            RNA polymerase, a kozak sequence, and a DNA sequence
            corresponding to amino acid numbers 1-25 of a human
            tau protein (xi) SEQUENCE DESCRIPTION: SEQ ID NO: 21:

GATCCCGCGA AATTAATACG ACTCACTATA GGGAGACCAC AACGGTTTCC CTCTAGAAAT       60
AATTTTGTTT AACTTTAAGA AGGAGATGCC ACCATGGTTG AGCCCCGCAT GGAGTTCG        118
```

(2) INFORMATION FOR SEQ ID NO: 22:

(i) SEQUENCE CHARACTERISTICS:
        (A) LENGTH: 30
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA (ix) FEATURE:
        (D) OTHER INFORMATION: a 5'-end region of T7 RNA
            polymerase including a part of a promoter thereof (xi) SEQUENCE DESCRIPTION: SEQ ID NO: 22:

GATCCCGCGA AATTAATACG ACTCACTATA                                  30

(2) INFORMATION FOR SEQ ID NO: 23:

(i) SEQUENCE CHARACTERISTICS:
        (A) LENGTH: 105
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA (ix) FEATURE:
        (D) OTHER INFORMATION: Spacer 5

(xi) SEQUENCE DESCRIPTION: SEQ ID NO: 23:

AAGCCACTCG CGTGGTCTCG CATTTTTTTT TTTTTTTTTT TTTTTTTTTT TTTTTTTTTT    60

TTTTTTTTTT TTTTTTTTTT TTTTTTTAA TGACCTCCCC TCTCC                      105

(2) INFORMATION FOR SEQ ID NO: 24:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA (ix) FEATURE:
        (D) OTHER INFORMATION: splint DNA (xi) SEQUENCE DESCRIPTION: SEQ ID NO: 24:

AAAGACAGTA AGGGAGAGGG GAGGT                                              25

(2) INFORMATION FOR SEQ ID NO: 25:

(i) SEQUENCE CHARACTERISTICS:
        (A) LENGTH: 47
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA (ix) FEATURE:
        (D) OTHER INFORMATION: a primer for reverse
            transcription PCR (xi) SEQUENCE DESCRIPTION: SEQ ID NO: 25:

-continued

```
GGTTTCCCTC TAGAAATAAT TTTGTTTAAC TTTAAGAAGG AGATATA                          47

(2) INFORMATION FOR SEQ ID NO: 26:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: other nucleic acid
        (A) DESCRIPTION: synthetic DNA (ix) FEATURE:
        (D) OTHER INFORMATION: a primer for reverse
            transcription PCR (xi) SEQUENCE DESCRIPTION: SEQ ID NO: 26:

AGCTTTCAGG CCAGCGTCCG TGTCA                                                  25
```